(12) United States Patent
Jensen

(10) Patent No.: US 7,113,940 B1
(45) Date of Patent: *Sep. 26, 2006

(54) COMPUTER-IMPLEMENTED PROCESS OF REPORTING INJURED WORKER INFORMATION

(76) Inventor: Michael E. Jensen, 211 N. Meridian St., Suite 201, Newberg, OR (US) 97132

( * ) Notice: Subject to any disclaimer, the term of this patent is extended or adjusted under 35 U.S.C. 154(b) by 0 days.

This patent is subject to a terminal disclaimer.

(21) Appl. No.: 09/557,878

(22) Filed: Apr. 24, 2000

Related U.S. Application Data

(63) Continuation of application No. 08/684,217, filed on Jul. 19, 1996, now Pat. No. 6,065,000.

(60) Provisional application No. 60/001,281, filed on Jul. 19, 1995.

(51) Int. Cl.
*G06F 17/60* (2006.01)

(52) U.S. Cl. ............... 707/3; 705/7; 705/11; 707/4; 707/10

(58) Field of Classification Search ............ 705/7, 705/10, 11; 707/10, 102, 3, 4; 715/505–508, 715/526, 530
See application file for complete search history.

(56) References Cited

U.S. PATENT DOCUMENTS

| | | | |
|---|---|---|---|
| 4,347,568 A | 8/1982 | Giguere et al. | |
| 5,291,399 A | 3/1994 | Chaco | |
| 5,299,121 A | 3/1994 | Brill et al. | |
| 5,521,815 A | 5/1996 | Rose, Jr. | |
| 5,586,024 A | 12/1996 | Shaibani | |
| 5,664,112 A | 9/1997 | Sturgeon et al. | |
| 5,726,884 A * | 3/1998 | Sturgeon et al. | 705/9 |
| 5,752,054 A * | 5/1998 | Garber et al. | 715/506 |
| 5,793,882 A | 8/1998 | Piatek et al. | |
| 5,884,275 A | 3/1999 | Peterson et al. | |
| 5,893,070 A * | 4/1999 | Garber et al. | 705/2 |
| 6,097,995 A * | 8/2000 | Tipton et al. | 700/266 |
| 6,604,808 B1 * | 8/2003 | King et al. | 705/4 |

FOREIGN PATENT DOCUMENTS

JP         57028370     * 2/1982

OTHER PUBLICATIONS

"New Version of Abra 2000 Human Resource Software Keeps Track of OSHA", News Release, May 20, 1990 [retrieved Apr. 19, 2005], 1 page, retrieved from: Dialog, file 16.*

(Continued)

*Primary Examiner*—Romain Jeanty
*Assistant Examiner*—B. Van Doren
(74) *Attorney, Agent, or Firm*—Kolisch Hartwell, P.C.

(57) ABSTRACT

Predefined lists of selected variables are created and interrelated to produce incident reports. The lists are created and modified through the use of formatted computer screens or input forms, and the reports are produced through the use of formatted computer outputs or output formats. The lists include accident-related information such as industry types, occupations, safety teams, attendance codes, types of injuries, body parts affected, types of incidents, site conditions, accident causes and safety reminders. The input forms often correspond directly to the types of lists, so that there is a form through which the list of industry types is created and/or modified, and another form through which the list of occupations is created. In addition, there are input forms that allow creation and/or modification of several lists at one time, particularly when each element in one list is directly associated with one element from another list. The output formats include agency-related formats such as an OSHA (Occupational Safety & Health Administration) No. 200 report, and statistical summaries used for managerial decision making. The statistical summaries may be textual or graphical, or a combination of textual and graphical.

1 Claim, 67 Drawing Sheets

OTHER PUBLICATIONS

Blotzer, Michael, "OSHA RecordKeeping and worker's compensation", Occupational Hazards, Oct. 1994 [retrived Apr. 19, 2005], vol. 56, Iss. 10, pp. 1-4, retrieved from: Proquest Direct.*

Morris, Jim, "Work Injuries, illnesses also watched by OSHA", Houston Chronicle, Dec. 26, 1994 [retrieved Apr. 19, 2005], pp. 1-2, retrieved from: Proquest Direct.*

Ness, Yan, "'Number-Crunching' Software persuades management to expand safety budget", Occupational Health and Safety, Apr. 1994 [retrieved Apr. 19, 2005], vol. 63, Iss, 4, pp. 1-2, retrieved from: Proquest Direct.*

Chen, Jacob Jen-Gwo, et al., "An ergonomic anaylsis system for laundry industries", Computers & Industrial Engineering, Jul. 1994 [retrieved on Apr. 19, 2005], vol. 26, Iss. 3, 1 page, retrieved from: Proquest Direct.*

Wrench, Constance, "Software Review: MicroHealthware-Corporate Health Resources, Inc.", American Industrial Hygiene Association Journal, Feb. 1993 [retrieved Apr. 19, 2005], vol. 54, Iss. 2, pp. 1-4, retrieved from: Proquest Direct.*

"Integrated Compliance Software for Employee Records", News Release, Aug. 12, 1991 [retrieve Apr. 19, 2005], pp. 1-3, retrieved from: Dialog, file 16.*

"Information System Beef up analysis of risk and benefits", Business Insurance, Apr. 18, 1994 [retrieved Apr. 19, 2005], pp. 1-4, retrieved from: Dialog, file 16.*

* cited by examiner

Fig. 4A1

| BUREAU OF LABOR STATISTICS<br>LOG AND SUMMARY OF OCCUPATIONAL<br>INJURIES AND ILLNESSES | | | |
|---|---|---|---|
| NOTE:<br>THIS FORM IS REQUIRED BY PUBLIC LAW 91-596 AND MUST BE KEPT IN THE ESTABLISHMENT FOR 5 YEARS. FAILURE TO MAINTAIN AND POST CAN RESULT IN THE ISSUANCE OF CITATIONS AND ASSESSMENTS OF PENALTIES. (*SEE POSTING REQUIREMENTS ON THE OTHER SIDE OF FORM.*) | | | |
| CASE OR FILE NUMBER | DATE OF INJURY OR ONSET OF ILLNESS | EMPLOYEE'S NAME | OCCUPATION |
| ENTER A NONDUPLI-CATING NUMBER WHICH WILL FACILITATE COM-PARISONS WITH SUPPLE-MENTARY RECORDS. | ENTER MO./DAY | ENTER FIRST NAME OR INITIAL, MIDDLE INITIAL, LAST NAME | ENTER REGULAR JOB TITLE, NOT ACTIVITY EMPLOYEE WAS PERFORMING WHEN INJURED OR AT ONSET OF ILLNESS. IN THE ABSENCE OF A FORMAL TITLE, ENTER A BRIEF DESCRIPTION OF THE EMPLOYEE'S DUTIES. |
| (A) | (B) | (C) | (D) |

Fig. 4A2

| | |
|---|---|
| RECORDABLE CASES: YOU ARE REQUIRED TO RECORD INFORMATION ABOUT EVERY OCCUPATIONAL DEATH, EVERY NONFATAL OCCUPATIONAL ILLNESS, AND THOSE NONFATAL OCCUPATIONAL INJURIES WHICH INVOLVE ONE OR MORE OF THE FOLLOWING: LOSS OF CONSCIOUSNESS, RESTRICTION OF WORK OR MOTION, TRANSFER TO ANOTHER JOB, OR MEDICAL TREATMENT (OTHER THAN FIRST AID). *(SEE DEFINITIONS ON THE OTHER SIDE OF FORM.)* | |
| DEPARTMENT | DESCRIPTION OF INJURY OR ILLNESS |
| ENTER DEPARTMENT IN WHICH THE EMPLOYEE IS REGULARLY EMPLOYED OR A DESCRIPTION OF NORMAL WORKPLACE TO WHICH EMPLOYEE IS ASSIGNED, EVEN THOUGHT TEMPORARILY WORKING IN ANOTHER DEPARTMENT AT THE TIME OF THE INJURY OR ILLNESS | ENTER A BRIEF DESCRIPTION OF THE INJURY OR ILLNESS AND INDICATE THE PART OR PARTS OF BODY AFFECTED<br><br>TYPICAL ENTRIES FOR THIS COLUMN MIGHT BE: AMPUTATION OF 1$^{ST}$ JOINT RIGHT FOREFINGER; STRAIN OF LOWER BACK; CONTACT DERMATITIS ON BOTH HANDS; ELECTROCUTION-BODY |
| (E) | (F) |
| ///////// | PREVIOUS PAGE TOTALS |
| | |
| | |
| | TOTALS (INSTRUCTIONS ON OTHER SIDE OF FORM) |

Fig. 4B1

| | |
|---|---|
| COMPANY NAME | |
| ESTABLISHMENT NAME | |
| ESTABLISHMENT ADDRESS | |

| EXTENT OF AND OUTCOME OF INJURY ||||||
|---|---|---|---|---|---|
| FATALITIES | NOFATAL INJURIES |||||
| INJURY RELATED | INJURIES WITH LOST WORKDAYS |||||
| ENTER DATE OF DEATH  MO/DAY/YR | ENTER A CHECK IF INJURY INVOLVES DAYS AWAY FROM WORK, OR DAYS OF RESTRICTED WORK ACTIVITY, OR BOTH | ENTER A CHECK IF IF INJURY INVOLVES DAYS AWAY FROM WORK | ENTER NUMBER OF DAYS AWAY FROM WORK | ENTER NUMBER OF DAYS OF RESTRICTED WORK |
| (1) | (2) | (3) | (4) | (5) |
| | | | | |
| | | | | |
| | | | | |
| | | | | |
| | | | | |
| | | | | |
| | | | | |
| | | | | |

| CERTIFICATION OF ANNUAL SUMMARY TOTALS BY _____ |
|---|
| OSHA NO. 200     POST ONLY THIS PORTION OF THE LAST PAGE |

Fig. 4B2

| FOR CALENDAR YEAR 19__ | PAGE ___ OF ___ |
|---|---|

| TYPE, EXTENT OF, AND OUTCOME OF ILLNESS ||||||||
|---|---|---|---|---|---|---|---|
| TYPE OF ILLNESS ||||||||
| INJURIES WITHOUT LOST WORKDAYS | CHECK ONLY ONE COLUMN FOR EACH ILLNESS (SEE OTHER SIDE OF FORM FOR TERMINATIONS OF PERMANENT TRANSFERS.) |||||||
| ENTER A CHECK IF NO ENTRY WAS MADE IN COLUMNS 1 OR 2 BUT THE INJURY IS RECORDABLE AS DEFINED ABOVE | OCCUPATIONAL SKIN DISEASE OR DISORDERS | DUST DISEASE OF THE LUNGS | RESPIRATORY CONDITIONS DUE TO TOXIC AGENTS | POISONING (SYSTEMIC EFFECTS OF TOXIC MATERIALS) | DISORDERS DUE TO PHYSICAL AGENTS | DISORDERS ASSOCIATED WITH REPEATED TRAUMA | ALL OTHER OCCUPATIONAL ILLNESSES |
|  | (7) |||||||
|  | (a) | (b) | (c) | (d) | (e) | (f) | (g) |
| (6) |  |  |  |  |  |  |  |
|  |  |  |  |  |  |  |  |
|  |  |  |  |  |  |  |  |
|  |  |  |  |  |  |  |  |
|  |  |  |  |  |  |  |  |
|  |  |  |  |  |  |  |  |
|  |  |  |  |  |  |  |  |
|  |  |  |  |  |  |  |  |
|  |  |  |  |  |  |  |  |

| TITLE _____ DATE _____ |
|---|
| NO LATER THAN FEBRUARY 1 |

Fig. 4B3

| | | FORM APPROVED O.M.B. NO. 1220-0029 |
|---|---|---|

| FATALITIES | NONFATAL ILLNESS | | | | |
|---|---|---|---|---|---|
| INJURIES RELATED | ILLNESS WITH LOST WORKDAYS | | | | ILLNESSES WITHOUT LOST WORKDAYS |
| ENTER DATE OF DEATH<br><br>MO/DAY/YR | ENTER A CHECK IF ILLNESS INVOLVES DAYS AWAY FROM WORK, OR DAYS OF RESTRICTED WORK ACTIVITY, OR BOTH. | ENTER A CHECK IF ILLNESS INVOLVED DAYS AWAY FROM WORK | ENTER NUM- BER OF DAYS AWAY FROM WORK | ENTER NUMBER OF DAYS OF RE- STRICTED WORK ACTIVITY | ENTER A CHECK IF NO ENTRY WAS MADE IN COLUMNS 8 OR 9 |
| (8) | (9) | (10) | (11) | (12) | (13) |
| | | | | | |
| | | | | | |
| | | | | | |
| | | | | | |
| | | | | | |
| | | | | | |
| | | | | | |
| | | | | | |

FIG. 7
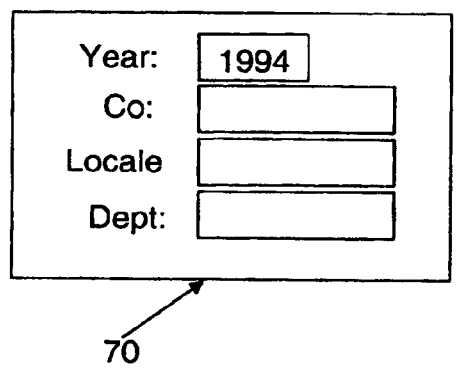
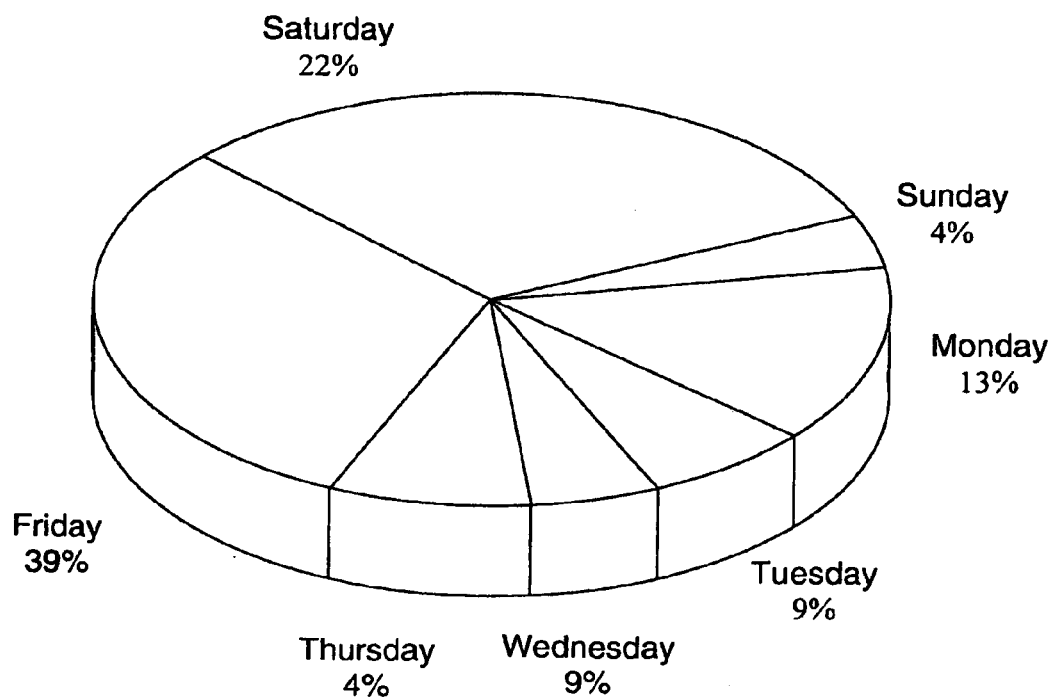
Accident Analysis – By Day of the Week

Fig. 8

SOS REPORT - STATUS REPORT
REPORT DATE

| REPORT ID/INFO: | | NATURE | DATE | C. ACTION | SUPVR. ACTION | ACTION ND | CAUSE | P. ACTION | ACKNOWL | COMPLTD |
|---|---|---|---|---|---|---|---|---|---|---|
| 1089 | GRANT NEAR MISS ON 3/14/94 | | | | | | | | | |
| 1901 | CHAISE UNSAFE ACT ON 5/1/94 | | | | | | | | | |
| 108875 | WALLER BREAK ON 5/14/94 | | | | | | | | | |
| 1005 | COLE UNSAFE ACT ON 5/14/94 | | | | | | | | | |
| 1698 | JEFFERSON ON 1/18/95 | | | | | | | | | |

INITIAL REPORT

INVESTIGATION

SAFESTAR-MASTER LIST ALL
  PARTICIPANTS (ALPHA)
  REPORT DATE: 11-JULY-95

VITAL STATISTICS:

| NAME: | BOYNTON, SUSAN |
|---|---|
| ADDRESS: | 13201 NE 44TH STREET #44 |
| CITY/ST/ZIP: | VANCOUVER, WA 98682 |
| PHONE: | 206-896-9726 |

EMPLOYMENT INFORMATION:

| SOC. SEC # | 5409629444 |
|---|---|
| D.O.B. | 8/3/64 |
| HIRED/LOE: | 5/12/76 - 19 YRS 2 MOS |
| DEPT# NAME | 3 - TRUCKING |

VITAL STATISTICS:

| NAME: | CHAISE, CHEVY |
|---|---|
| ADDRESS: | 499 FOX BLVD. |
| CITY/ST/ZIP: | HOLLYWOOD, CA 76004 |
| PHONE: | 310-655-7324 |

EMPLOYMENT INFORMATION:

| SOC. SEC # | 545069823 |
|---|---|
| D.O.B. | 5/17/47 |
| HIRED/LOE: | 4/11/78 - 17 YRS 3 MOS |
| DEPT# NAME | 2 - OFFICE |

VITAL STATISTICS:

| NAME: | GRANT, LOU |
|---|---|
| ADDRESS: | 497 WRITERS DR. |
| CITY/ST/ZIP: | PERIODICAL, NE 97640 |
| PHONE: | 402-555-2222 |

EMPLOYMENT INFORMATION:

| SOC. SEC # | 789879742 |
|---|---|
| D.O.B. | 12/2/40 |
| HIRED/LOE: | 6/14/90 5 YRS 1 MOS |
| DEPT# NAME | 5 - RETAIL |

VITAL STATISTICS:

| NAME: | JEFFERSON, GEORGE |
|---|---|
| ADDRESS: | 804 HIGH RISE BLVD |
| CITY/ST/ZIP: | NEW YORK, NY 80754 |
| PHONE: | 201-555-6890 |

EMPLOYMENT INFORMATION:

| SOC. SEC # | 773901320 |
|---|---|
| D.O.B. | 8/13/58 |
| HIRED/LOE: | 7/18/88 - 7 YRS 0 MOS |
| DEPT# NAME | 1 - MANUFACTURING |

Fig. 10A

ACCIDENT REPORT SYNOPSIS BY PERIOD
REPORT DATE: 11-JUL-95

| REPORT START | 01-JAN-94 | REPORT END | 01-JAN-95 |
|---|---|---|---|

MONTH JANUARY

| DEPARTMENT | 1 - MANUFACTURING |
|---|---|

| INJURY DATE | LAST NAME | FIRST | SSN | NATURE OF INJURY | ACCIDENT TYPE | LOE | TIME IN DEPT |
|---|---|---|---|---|---|---|---|
| 1/14/94 | KEATON | BUSTER | 812902231 | THERMAL & CHEMICAL | LOCK OUT/TA | 1 YRS-10 MOS | |
| ACCIDENT DESCRIPTION | WHEN A DOOR TO THEM MAIN FURNACE WAS OPENED ACCIDENTALLY, EMPLOYEE'S RIGHT ARM WAS BURNED WHEN THE FURNACE LOCK-OUT / TAG-OUT SWITCH FAILED TO ENGAGE | | | | | | |
| CORRECTIVE ACTION TAKEN | HAVE SHUT DOWN THE FURNACE AND ORDERED REPAIRS MADE. ALSO, HAVE ADVISED EMPLOYEE OF CORRECT PROCEDURE. | | | | | | |

MONTH FEBRUARY

| DEPARTMENT | 1 - MANUFACTURING |
|---|---|

| INJURY DATE | LAST NAME | FIRST | SSN | NATURE OF INJURY | ACCIDENT TYPE | LOE | TIME IN DEPT |
|---|---|---|---|---|---|---|---|
| 2/11/94 | JEFFERSON | GEORGE | 773901320 | RN-CHEMICAL/ILLN | HAZARDOUS M | 6 YRS - 4 MOS | |

Fig. 10B

| INJURY DATE | LAST NAME | FIRST | SSN | NATURE OF INJURY | ACCIDENT TYPE | LOE | TIME IN DEPT |
|---|---|---|---|---|---|---|---|
| 2/11/94 | KEATON | BUSTER | 813902231 | HEARING LOSS/INJURY | HEARING PROT. | 2 YRS - MOS | |

| ACCIDENT DESCRIPTION | EMPLOYEE BURNED ARM WITH ACID |
|---|---|
| CORRECTIVE ACTION TAKEN | |

| ACCIDENT DESCRIPTION | EMPLOYEE RECEIVED HEARING INJURY DUE TO FAILURE TO WEAR HEARING PROTECTION PROPERLY |
|---|---|
| CORRECTIVE ACTION TAKEN | HAVE ADVISED CORRECT PROCEDURE |

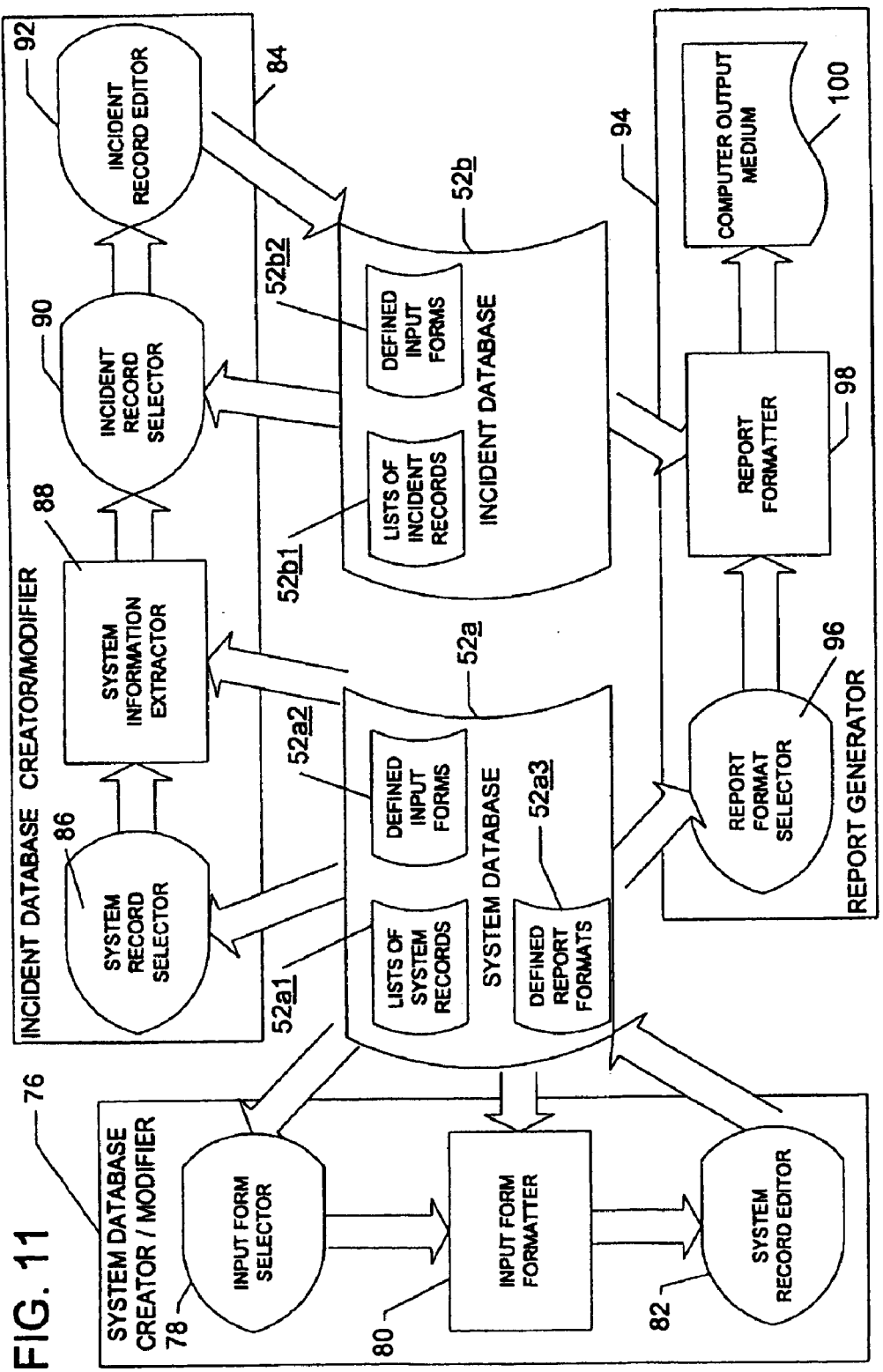

Fig. 18

Sign-On Permissions

LOOKUP: [    ]  [⇧][◀][▶][▶|]  [EDIT] [DELETE] [ADD] [CLOSE]

Instructions: To Add/Modify/Delete a permissions record, follow these steps
Step #1: Sign-On ID= Any letter / number combination
that identifies the user (required)
Step #2: Password = Any letter / number combination (no spaces) that acts as
a secondary security level (e.g. dept. name, file name, etc.)
Step #3: Company = Select a specific company name from the list or leave
the "*" if unlimited access is desired, (note: the "*" is the default
value, if you want to restrict the records for this user to a specific
company you will need to replace the "*" with a company name
Step #4: Level = Within a given company, Select a specific plant/location #
from the list, or leave "*" if unlimited access is desired. (Same note
applies as for the company. see Step #3)

[ Master Password ]

[ Change Master Password ]

| Sign-On ID | Password | Company | Level |
|---|---|---|---|
|  |  | * | * |
|  |  | * | * |

Fig. 23

Company Setup

Save | Close | Add | Open Dept. Setup Form | Confiture Printer Now

Company Name

Address

Address

City | ST | ZIP | County | Telephone

Locator # | 999 | State of Op: | | Gen. Mgr. or Pres.

General Nature of Business:

Industry: | SIC Code:

Primary Hospital: | Of Record

Page Down | Page Bottom

Workers Comp. Insurance Info. | State Workers Comp. Division Info.

Fig. 24

| Body Part - Entry Form | |
|---|---|
| EDIT ADD DELETE CLOSE | |
| Body Part | Code |
| ▶ Abdomen (Includes Internal Organs) | 515 |
| Ankle(s) | 520 |
| Arm(s) | 507 |
| Back (lower, Mid, Upper) | 513 |

Fig. 28

| | Counter |
|---|---|
| LAST | Text |
| FIRST | Text |
| SSN | Number |
| Birthday | Date/Time |
| LOE | Text |
| ADJ | Date/Time |
| Address | Text |
| City | Text |
| State | Text |
| Zip | Number |
| PHONE | Text |
| DEPT | Text |
| Dept Name | Text |
| Company | Text |
| Locale | Text |
| HrlyRate | Number |
| Occupation | Text |
| | Text |

Fig. 25

Master Enrollment Form

LOOKUP: [ ] ⇩ |◄◄|◄|►|►►| EDIT DELETE NEW CLOSE

ID: [ ]

Company Name: [ ] Location: [ ] ⇩ *Required Only for Network Installations*

Last: [ ] First: [ ] Social Security #: [ ] Date of Birth: [ ]

Address: [ ]

City: [ ] State: [ ] Zip: [ ] Phone Number: [ ]

Debit Code: [ 2 ] ⇩ Dept. Name: [ OFFICE ] Supervisor: [ ] ⇩ Occupation: [ ] Hourly Rate: [ $10.00 ] Date of Hire: [ 4/11/78 ]

Team Code: [ 5 ] ⇩ Team Name: [ FALCONS ] *Complete if Safety Awareness Program will be used and based on "Team" Performance.* Length of Employment: [ 6yrs. 11mos ]

Fig. 26

ATTENTION! VERY IMPORTANT INFORMATION

You have selected the IMPORT function of the program.

In the event that you continue without completing all of the required steps and are exited out of the program, be assured that your data will not be lost. However, you will need to restart the program.

Note: You should invoke this function only if you have all of the information required and are ready to import the selected ASCII or Excel Spreadsheet file into the program.

In order for this process to be preformed successfully, the file you are preparing to import MUST BE in the EXACT column and date-type order as the Table you are importing into. If this is not done, unrepairable errors may occur and your imported data will not be complete, or may be imported into the incorrect fields of the Table [eg. Social Security # imported into the LAST name column.]

If you are unsure or need additional information, select the requested Table name and press the PRINT TEMPLATE button, before continuing Table Template Selection

[ PRINT TEMPLATE ]　[ CANCEL ]　[ CONTINUE ]

Fig. 27

Important Setup Parameters

Select the Source Type of the Data Being Imported
- ○ Text Delimited [ASCII]
- ○ Excel Spreadsheet
- ○ Lotus WKS file
- ○ Lotus WK1 [Version2]
- ○ Lotus WK3 [Versions 3 & 4]

Enter Full Path Name of Data to be Imported

Enter Name of Table to Import Data Into

Does the First Row Contain Field Names   ☐ YES  ☐ NO

Replace All of the Existing Records?   ☐ YES  ☐ NO

*Press CLOSE when the import function is completed. (The hour glass will disappear and the floppy drive light will go off.)*

OK     CLOSE

Fig. 29

| Export Setup Parameters | |
|---|---|
| Check Here to Confirm Export | [O] |
| Enter Name of Table to Export | [⬇] |
| Enter Full Path Name of Data Destination (incl. drive specifications, directory name & file name eg. C:\excel\JanAcc.txt) | |

[OK]  [CLOSE]

Fig. 32

| | |
|---|---|
| Open Claim? | ☐ |
| Disabling Claim? | ☐ |
| Investigation Required? | ☐ |

Fig. 33

| | | |
|---|---|---|
| is a "First Report of Injury" Required? | ☒ Yes | ☐ No |

Fig. 30

Accident Form

RECORD LOOKUP: [____] [⇩] [⫷⫷⫸⫸] [EDIT] [DELETE] [NEW] [CLOSE] [OVERRIDE]  Accident #: [__82__]

Vital Information

Emp. ID: [1234567] [⇩]  Soc. Sec. Number: [123-45-6789] [⇩]  Name Lookup: [_____] [⇩]

Last: [_____]  First: [_____]  Birthdate: [____]  Sex: ☐ Male  ☐ Female

Address: [_____]  City: [_____]  State: [__] Zip: [____]

2/14/77  17 YRS. 8 MOS.  [999]  Location [_____]  Phone Number: [_____]
Adj. Hire Date:  L.O.E.:  Company: [_____]

JANITOR  Dept. #: [2]  Department Name: [OFFICE]  Time in Dept. [_____]
Worker Occupation Team Code: [6]  Team Name: [BlueJays]

[Page Down]  [Accident Specifics]  [Page Bottom]  [OSHA Info.]

Fig. 31

Accident Specifics  Date of Injury: 2/11/95   Time of Injury: ☐

Hospitalized: ☐ YES ☒ NO   Hospital: ☐   Physician: ☐

Body Part Afflicted: ☒ RIGHT  ☐ LEFT   Body Part Previously Injured? ☐ YES ☒ NO
WRIST(S) ▼                                If Yes, Explain:

Nature of Injury: FRACTURE ▼   Incident Type: ▼

Contrib. Cause: HORSEPLAY ▼   Conditions: POOR LIGHTING ▼

Adv. Info.                     Awareness Code: SLIPS & FALLS ▼

Company Accident Description

Corrective Action Taken

Date Completed:    Is a "First Report of Injury" Required? ☒ YES ☐ NO

☐ Open Claim?
☐ Disabling Claim?         Page Up      Vital Statistics      Page Down      FROI & OSHA Info.
☒ Investigation Required?

Fig. 34

Accident Report - Advanced Information

Reference:

Primary Cause.
HORSEPLAY

Secondary Causes
Caught in, Under, Between

Summary:
Confined Space
Excessive Exposure

Primary Condition.
POOR LIGHTING

Secondary Conditions:
EXCESSIVE EXPOSURE

Summary:

Primary Witness.
[Return]

Supplemental Witnesses:

Summary:

Fig. 35

Employee Accident Description If version does not differ from Co. Description, copy & paste from above Witness:

Date Co. Knew:

Street Address of Accident:

County of Injury:

Injured on Premises?
☒ YES ☐ NO

Injured While on the Job?
☒ YES ☐ NO ☐ UNKNOWN

Other Workers Injured?
☐ YES ☒ NO

Did someone else cause accident?
☐ YES ☒ NO

Was accident caused by failure of machinery or product?
☐ YES ☒ NO

Fatality?
☐ YES ☒ NO

Is worker an Owner of Officer?
☐ YES ☐ NO

Working Shift Start:

Working Shift End:

Date Worker Left:

Time Worker Left:

Date Worker Returned:

Number Hrs. Per Shift: 8

Days per week worked:
3 or Less  4  5  6  7
    ☐     ☐  ☐  ☐  ☐

Scheduled Days Off:
S  S  M  T  W  T  F
☒  ☐  ☒  ☐  ☐  ☐  ☐

Wage: $9.00
☒ Hr.  ☐ Wk.  ☐ Yr.
☐ Day  ☐ Mo.

Page Up

Accident Specifics

Page Top

Vital Statistics

Page Down

OSHA 200 LOG Entry

Fig. 36

First Report of Injury - State Exceptions

In addition to the information already provided, your state also requires the following: [RETURN]

OSHA CASE #: [ ]    Employee Policy #: [ ]

Case #: [ ]    Was Salary Continued?: ☐ YES ☒ NO

Employee Class Code: [ ]

Value of other payments not recorded: [ ]    Paid full wages for day of Injury?: ☐ YES ☒ NO Gross Wages/Salary: [ ]

Employer Type: [ ]    If a fatality, what is the date of death?: [ ]

Hospital Address: [ ]
Physician's Address: [ ]

What was worker doing at the time of Injury?: [ ]    What equipment /material was the employee using during time of Injury?: [ ]

Fig. 39

| Injury Related | | | | | |
|---|---|---|---|---|---|
| | Nonfatal Injuries | | | | |
| Fatalities | | Injuries With Lost Work Days | | | Injuries Without Lost Workdays |
| Injury Related<br><br>Enter DATE of death.<br><br>Mo/da/yr | Enter a CHECK if injury involves days away from work, or days of restricted work activity or both. | Enter a CHECK if injury involves days away from work. | Enter number of DAYS away from work. | Enter number of DAYS of restricted work activity. | Enter a CHECK if no entry was made in columns 1 or 2 but the injury is recordable as defined above. |
| (1) | (2) | (3) | (4) | (5) | (6) |
| ☐ | ☐ | ☐ | ☐ | ☐ | ☐ |

[PAGE TOP] [Vital Statistics] [PAGE UP] [OSHA 200 LOG Info.]

Fig. 40

| (7) Type of Illness  *Check only one column for each illness* | | | | | |
|---|---|---|---|---|---|
| Occupational Skin Diseases or Disorders ☐ (a)     Disorders Due to Physical Agents ☐ (e) <br> Dust Diseases of the Lungs ☐ (b)     Disorders Associated with Repeated Trauma ☐ (f) <br> Respiratory Conditions Due to Toxic Agents ☐ (c)     All Other Occupational Illnesses ☐ (g) <br> Poisoning (systemic effects of toxic materials) ☐ (d) | | | | | |

| Illness Related | | | | | |
|---|---|---|---|---|---|
| Fatalities | Nonfatal Illnesses | | | | Illnesses Without Lost Workdays |
| | | Illness With Lost Work Days | | | |
| Illness Related Enter DATE of death. Mo/da/yr | Enter a CHECK if illness involves days away from work, or days of restricted work activity or both. | Enter a CHECK if illness involves days away from work. | Enter number of DAYS away from work. | Enter number of DAYS of restricted work activity. | Enter a CHECK if no entry was made in columns 1 or 2 but the illness is recordable as defined above. |
| (8) ☐ | (9) ☐ | (10) ☐ | (11) ☐ | (12) ☐ | (13) ☐ |

Fig. 41

Advanced Accident Investigation:

RECORD LOOKUP: [ ] ⬇ ⏮◀▶⏭ CLOSE    Accident ID [ 86 ]

Report Overview    Enter any investigation report #  [ 5342 ]

Name: [ ]  SSN: [ ]  DOB: [ ]  Trucking  Dept. Name: [ ] Company
☐ Male                                  6 months  [ 999 ]
☐ Female                                Time in Dept.  Locale:

Date: [ 10/17/94 ]  Location: [ ]

Description  Employee's right arm was amputated

Report Status  Initial Report                                  Investigation

| Nature | Date | C.Action | BodyPart | Incid.Type | Cause | P.Action | Acknowl. | Completed |
|--------|------|----------|----------|------------|-------|----------|----------|-----------|
|        |      |          |          |            |       |          |          |           |
|        |      |          |          |            |       |          |          |           |
|        |      |          |          |            |       |          |          |           |
|        |      |          |          |            |       |          |          |           |

Incident Investigation    Training & Special Info.

Fig. 42

Investigation Support

| | | COUNT |
|---|---|---|
| WHAT | Break | 4 |
| WHERE | | 0 |
| WHAT KIND | | 0 |
| BODY PART | Arm(s) L☐ R☒ | 6 |
| HOW LONG? | | -TO- |

| | | | COUNT |
|---|---|---|---|
| WHEN | 10/17/94 | -AT- 8:00:00 a.m. | 2 |
| CONDITION | Confined Space | | 12 |
| HOW BAD? | FATALITY: ☐ | HOSPITALIZED: ☒ | |
| OSHA status | FROI to be Filed?: ☐ | | |
| | 200 Log Recordable? ☐ | | |

Accident Description: Employee's right arm was amputated.

Corrective Action Description: Nothing.

Corrective Action Taken: 10/18/94

⇩

Probable Root Cause: Hazard

Training & Special Info.

Report Overview

Fig. 43

Training History

| Class Name | Class Date: | Re-Training: |
|---|---|---|
| Basic CPR | 1/16/95 | 5/16/95 |
| Basic CPR | 5/17/94 | 9/14/94 |
| Basic CPR | 6/14/94 | 10/12/94 |

Investigation Notes: Employee determined to be incompetent.

Accident History

| Date | Nature of Injury | Body Part | Incident Type | Condition | Cause |
|---|---|---|---|---|---|
| 12/2/94 | Bruise | Ankle(s) | Struck By | Slippery Floor | Hazard |

Preventative Action Taken: Have changed policies re: accident procedures

Corrective Action Assigned to: _____ Date Completed: 1/15/09

Investigated By: _____

Performance Analysis

| 2 | 2 | 100.00% |
|---|---|---|
| Co. Avg. | Acc total this | Individual |
| #pp | Person | Performance |

Report Overview

Advanced Investigation

Fig. 44

Accident Related Information
Date of Corrective Action Entry Review Form
Lookup: [ ]  [⇩] [◀◀][◀][▶][▶▶]  [EDIT] [DELETE] [ADD] [CLOSE]

| Date of Injury | Name | Nature & Type of Injury | Corrective Action Taken |
|---|---|---|---|
| 1/8/97 | Employee Name | Bruise | |
| | | Lock Out / Tag Out | |
| 6/11/92 | Employee Name | Asphyxiation | |
| | | Respiratory Protection | |
| 4/11/93 | Employee Name | Eye | |
| | | Eye Protection | |
| 1/14/94 | Employee Name | Thermal/Chemical Burn | Have shut down the furnaces and ordered repairs made. |
| | | Lock Out / Tag Out | |
| 2/11/94 | Employee Name | Burn - Chemical/Illness | |
| | | Hazardous Materials | |

Fig. 45

TRAFFIC ACCIDENT AND INSURANCE REPORT  Accident # [ 3 ]

Lookup: [_____]  ⬇ ⏮ ◀ ▶ ⏭  [SAVE] [DELETE] [ADD] [CLOSE]

REPORT DIRECTORY

Employee Lookup: [_____]  Press to Select

Employee Name and SS# ⬇

VEHICLE #1  [Driver]  [Vehicle Info]

[Passengers]  [Insurance Info.]

VEHICLE #2  [Driver]  [Vehicle Info]

*If Accident involved someone outside of a motor vehicle, answer the following questions.*

INFORMATION OTHER: Involved Pedestrian ☐   Name: [_____]
Involved Bicyclist ☐   Address [_____]

Fig. 49

1ST Quarter

| January | February | March |
|---|---|---|
| 0 | 0 | 0 |

[OK] [Cancel]

Fig. 46

Department Status Change - Quick Entry Screen

Lookup: [____] |◀◀ ◀ ▶ ▶▶| [CLOSE]

| LAST | FIRST | SSN | DOB | HIRE | DEPT | Dept Name |
|---|---|---|---|---|---|---|
| Last-name | First-name | 123-45-6789 | 01/23/45 | 12/30/89 | 3 | Office |
| Last-name | First-name | 123-45-6789 | 01/23/45 | 12/30/89 | 3 | Office |
| Last-name | First-name | 123-45-6789 | 01/23/45 | 12/30/89 | 3 | Office |
| Last-name | First-name | 123-45-6789 | 01/23/45 | 12/30/89 | 3 | Office |
| Last-name | First-name | 123-45-6789 | 01/23/45 | 12/30/89 | 3 | Office |
| Last-name | First-name | 123-45-6789 | 01/23/45 | 12/30/89 | 3 | Office |

Fig. 47

Team Status Change -- Quick Entry Screen

Lookup: [_____] |◁ ◀ ▶ ▶| CLOSE

| LAST | FIRST | SSN | DOB | HIRE | CODE | Team Name |
|---|---|---|---|---|---|---|
| Last-name | First-name | 123-45-6789 | 01/23/45 | 12/30/89 | 4 | Eagles |
| Last-name | First-name | 123-45-6789 | 01/23/45 | 12/30/89 | 4 | Eagles |
| Last-name | First-name | 123-45-6789 | 01/23/45 | 12/30/89 | 4 | Eagles |
| Last-name | First-name | 123-45-6789 | 01/23/45 | 12/30/89 | 4 | Eagles |
| Last-name | First-name | 123-45-6789 | 01/23/45 | 12/30/89 | 4 | Eagles |
| Last-name | First-name | 123-45-6789 | 01/23/45 | 12/30/89 | 4 | Eagles |

Fig. 48

Monthly Safety Admin. - Hours Worked Entry Form

Year Lookup: [ ⇩ ] [◀◀][◀][▶][▶▶] [EDIT] [DELETE] [ADD] [CLOSE]

Company Name: [ ⇩ ] Plant Location#: [999]

Submitted To: [1] ⇩

THIS REPORT COVERS THE FISCAL YEAR LISTED BELOW:

[1993]

Authorization / Routing

Production Manager: [ ]  Purchasing Manager: [ ]  General Manager: [ ]

Select Quarter

[1st Quarter] [2nd Quarter] [3rd Quarter] [4th Quarter]

Fig. 50

S.O.S. Report Form

Lookup: [_____] ⬇  |◄◄ ◄ ► ►►|  EDIT  DELETE  ADD  CLOSE  OVERRIDE

Report Basics: Report ID [____] ⬇

Reported By: Company Employee ☐  Non Employee ☐

If reported by a company employee, use the "name lookup" box below, to select the person's name who is reporting Name Lookup: [_____] ⬇   [Last]   [First]

Mail Stop / Location [_____]   Address [_____]   City [____]  State [__]  Zip [__]  Phone [__]

Company [_____]

Affected Persons (If different than above i.e. contractor, visitor, etc.): [_____]

Page Down — Incident Specifics

Fig. 51

Incident Specifics

Date Observed: [    ]  Time: [10:00 A.M.]

Incident Location: [    ]  Incident Type: [Faulty Floor or Surface ▼]

Incident Nature: [Break ▼]  Conditions: [    ]

Witness: [    ]

Incident Description

[    ]

Corrective Action Taken [X] Yes [ ] No  *If Yes complete the following information*

Description: [    ]

Date Completed: [    ]

Did you involve your supervisor? [ ] Yes [ ] No  Their Name: [    ]

Is further action needed? [X] Yes [ ] No  If Yes, suggestions: [    ]

[Page Up]  Report Basics

Fig. 52

S.O.S. Investigation

Lookup: [____] [⊕] [◁◁ ◁ ▷ ▷▷] [CLOSE]

Report Overview | Report ID [1005]

Submitted By:
☐ Company Employee  ☐ Non Employee

Name [____]

Mail Stop / Location [____]  Address [____]  City [____]  State [____]  Zip [____]

Affected Persons: [____]

Description: [____]

Report Status

| Initial Report | | | | | Investigation | | | |
|---|---|---|---|---|---|---|---|---|
| Nature | Date | C.Action | Supvr. | Action Nd. | Cause | P.Action | Acknowl. | Completed |
|  |  |  |  |  |  |  |  |  |
|  |  |  |  |  |  |  |  |  |

[Incident Investigation]  [Action & Response]

Fig. 53

Training - Enrollment Form

Class Lookup: [▽]  [|◁ ◁ ▷ ▷|]  [EDIT] [DELETE] [ADD] [CLOSE]

| CODE: | CASS NAME: | SUBJECT: | Re-Training Interval: |
|---|---|---|---|
| CPR 101 | Basic CPR | Basic CPR Technique Training | Four Months [▽] |

Date: 5/17/94  Instructor: [____]  »Next Date: | Create New Date:
Location: [____]  Test ID: Advanced CPR [▽]  «Prev. Date: |

Attendees:

| | Name Lookup | Last | | Last | First Name | Dept. Name | Company | |
|---|---|---|---|---|---|---|---|---|
| ▲ | Full Name - SSN [▼] | Last Name | | | First Name | Office | Company Name | |
| | Full Name - SSN | Last Name | | | First Name | Office | Company Name | |
| | Full Name - SSN | Last Name | | | First Name | Office | Company Name | |
| | Full Name - SSN | Last Name | | | First Name | Office | Company Name | |
| | Full Name - SSN | Last Name | | | First Name | Office | Company Name | |

Record: |◁ ◁| 1 |▷ ▷|

Fig. 54

RE-TRAINING -- Enrollment Form

Class Lookup: [ ⬇ ]  [ ⏮ ◀ ▶ ⏭ ]  [ CLOSE ]

| CODE: | CLASS NAME: | SUBJECT: | Re-Training Interval: |
|---|---|---|---|
| CPR 101 | Basic CPR | Basic CPR Technique Training | Four Months ⬇ |

Date: 4/1/94

Instructor: [ ] ⬇

Test ID: [ ]

[ >>Next Date: ]  [ Create New Date: ]
[ <<Prev. Date: ]

Location: [ ]

Attendees:

| Name Lookup | Last | Last | Dept. Name | Company |
|---|---|---|---|---|
| ➡ | | | | ⬆ |
| | | | | |

[ ⏮ ◀ ▼ ] Record: 1

Fig. 55

Create or
Modify a test

Locate a Specific Test

[ 🔍 ] or [ New ]

Test Name  [ Advanced CPR ]

Test Subject  [ Advanced CPR Training ]

Question: [ When performing CPR, what is the correct ratio of "breaths" to "beats?" ]  ▼

Points [ 10 ]   Type [ B ]

[ Previous Question ]
[ Next Question ]

ANSWERS
○ A. 5 breaths to 2 beats
⦿ B. 2 breaths to 5 beats
○ A. 4 breaths to 3 beats

Fig. 56

Score a Test

Session ID: [CPR 101 ▼]

Test: [Advanced CPR ▼]   [Go to Test Entry Screen]

Student: [_____ ▼]   [Close]

| Number | Answer | Score | Question | Correct Responses |
|--------|--------|-------|----------|-------------------|
| 1 | 2 | 10 | When performing CPR, what is the | (2 10) B,2 breaths to 5 Beats |
| 2 | 1 | 0 | Before performing CPR, you should | (2 10) FALSE |
| 3 | 1 | 10 | You should open a victim's mouth | (1 10) TRUE |
| 4 | 1 | 10 | How long should you continue the | (1 10) A - Until professional m |
| 0 | 1 |  |  |  |

[4 Questions] [30 Points Total]

Fig. 57

Test Question Summary

Test: Advanced CPR
Advanced CPR Training

[Modify This Test] [Close]

| # | Question | Answer | Points |
|---|---|---|---|
| 1 | When performing CPR, what is the correct ratio of for "b | B. 2 breaths to 5 Beats | 10 |
| 2 | Before performing CPR, you should move the person | FALSE | 10 |
| 3 | You should open a victim's mouth and check for obstruct | TRUE | 10 |
| 4 | How long should you continue the procedure once it i | A. Until professional medical | 10 |

Fig. 58

Cost of Accident

Lookup: [CLOSE]

Vital Information

Last: _____  First: _____

Date of Birth: 5/14/47    Soc. Sec. #: _____

Accident Report Recap:

Date of Injury: 10/17/94    Nature of Injury: Break    Body Part: Arm(s)    Accident Type: Lock Out / Tag Out    Fatality? ☐

Description: Employee's right arm was amputated.

Accident Costs:

Direct Medical Costs: $500.00
Compensation Costs: $100.00
Administration Costs: $120.00
Initial Accident Costs: $720.00
Estimated Reserves: $2,000.00

Fig. 59

Worker's Compensation Analysis - Setup Form

| Name of Primary Product | Plastics |
| Avg. Retail Cost per Unit | $15,000.00 |
| Avg. % of Profit per Unit | 20.00% |
| # Mfg. Days Req. per Unit | 1 |

CLOSE

Record: 1

Fig. 60

Advanced Tracking - Entry Screen

LOOKUP: [ ⇩ ]   [|◀] [◀] [▶] [▶|]   [EDIT] [DELETE] [ADD] [CLOSE]

Soc. Sec. Number: [ ⇩ ]   Name Lookup:

[_____]   [_____]
Last             First

[7/1/77]   [17yrs-3mos]   [5]   [Retail]
Adj. Hire Date:   L.O.E.:   Dept. #:   Dept. Name:

Date Absent: [1/13/94]   Date Returned: [1/28/94]   Absence Code: [Unexcused] [⇩]

Corrective Action [X]   Corrective   [Associate placed on notice of suspension
Required?                Action Taken:  of privileges                              ]

Fig. 61

OSHA 200 Information

Record Lookup: [ ]  ▼▲◄► CLOSE DELETE

Enter a Case Number: [ ]

Vital Information

Name: [ ]

Date of Birth: 5/17/47    Soc. Sec. #: [ ]    Date of Injury: 12/2/94

Date of Hire: 6/18/81    L.O.E.: 13yrs - 6mos    Department: [ 5 ]    Retail

Dept. Name:

Time in Dept: [ ]    Occupation: Supervisor

Accident Recap | Injury Related | Illness Related

Fig. 62

Accident Report Recap:

| WHAT | Fracture | Wrist(s) | ☐ LEFT ☒ RIGHT |

| WHEN | 12/17/94 | HOW LONG | | |

HOW BAD ☐ FATALITY?    Date Left:    Date Returned:

Company Accident Description

Enter a Unique Case Number:

Push to enter info in Correct Category

| Injury Related | Illness Related |

OSHA 200 Form Accident Description

| PAGE TOP | Vital Statistics | PAGE UP | FROI & OSHA Info. |

Fig. 66

OSHA - First Report of Injury

Select Accident File

CONFIRMATION

Last Name          Date of Injury

OPTIONS

| Print Preview | Print | CANCEL |

Fig. 63

| Injury Related | | | | | |
|---|---|---|---|---|---|
| Fatalities | Nonfatal Injuries | | | | |
| | Injuries With Lost Work Days | | | | Injuries Without Lost Workdays |
| Injury Related Enter DATE of death. Mo/da/yr | Enter a CHECK if injury involves days away from work, or days of restricted work activity or both. | Enter a CHECK if injury involves days away from work. | Enter number of DAYS away from work. | Enter number of DAYS of restricted work activity. | Enter a CHECK if no entry was made in columns 1 or 2 but the injury is recordable as defined above. |
| (1) | (2) | (3) | (4) | (5) | (6) |
| ☐ | ☐ | ☐ | 0 | ☐ | ☐ |

| PAGE TOP | Vital Statistics | PAGE UP | OSHA 200 LOG Info. |

Fig. 64

Accident Report by Period

Related Categories

Select report data criteria from any or all of the below listed categories

- Nature of Injury
- Accident Type
- Cause
- Condition
- Body Part

Report Period

Enter the report START and END dates

START          END

To further customize your report, one or all of the following may be selected

- Company
- ??? ???
- Department

OPTIONS

Print Preview     Print     CANCEL

Fig. 65

Accident Analysis - Parameter Defined

Report Period

Enter the report START and END dates

START    END

To further customize your report, one or all of the following may be selected

Company
???? ????
Department

Related Categories

Select report data criteria from any or all of the below listed categories

Nature of Injury
Accident Type
Cause
Condition
Body Part

OPTIONS

Print Preview    Print    CANCEL

Fig. 71

Accident Related Graphs

Enter Year to Process

Press to Select Multi-Yr Comparison

Options
- Preview
- Print
- Design

Description

To further customize your graphs, one or all of the following may be selected
- Company
- Division / Plant
- Department Select Graph to Open:
- ○ Accident Reminders     ○ ??? By Dept.
- ○ Body Parts
- ○ Costs / Hi to Lo
- ○ Departments
- ○ Freq. By Day of the Week
- ○ Freq. By Time of the Day
- ○ Injuries Avg. Cost
- ○ Length of Emp.
- ○ Monthly Totals
- ○ Nature of Injury

COMPUTER-IMPLEMENTED PROCESS OF REPORTING INJURED WORKER INFORMATION

CROSS-REFERENCE TO RELATED APPLICATIONS

This application is a continuation and claims priority from U.S. patent application Ser. No. 08/684,217 entitled COMPUTER-IMPLEMENTED PROCESS OF REPORTING INJURED WORKER INFORMATION filed on Jul. 19, 1996, now U.S. Pat. No. 6,065,000, which claims priority from U.S. Provisional Patent Application Ser. No. 60/001,281 entitled "INCIDENT REPORTING SYSTEM" filed on Jul. 19, 1995.

TECHNICAL FIELD

This invention relates generally to the organization, coordination and presentation of data related to workplace incidents such as accidents resulting in worker injuries. For example, the invention includes a method of prompting a user for information about the workplace such as employee identification, accident and injury classification, and educational and precautionary actions to be taken. The invention also includes a method of prompting a user for information necessary to complete accident reports of the type required by federal, state and local agencies, and reports useful for making managerial decisions about the workplace. The recording and reporting of statistics about such incidents is both necessary to comply with governmental regulations, and useful to evaluate and improve workplace safety. The present invention provides a system for the administration and support of the industry process known as light duty/restricted duty/recurrence of injury recording, analysis and reporting.

BACKGROUND ART

In the past, a myriad of paper and paperless forms have been developed and used to aid in this process. For example, OSHA (Occupational Safety & Health Administration) form No. 200 is a fill-in-the-blanks form, with blanks for specific information about a given accident, such as the name of the injured, the type of injury, the severity of the injury and the extent of any resulting absence from work. While it is relatively simple for a user to complete the form, only the most experienced user is able to complete the form with any type of standardization. Furthermore, it is difficult to coordinate such standardization among disparate users, as is desirable in a large, multi-plant workplace. Computer databases have also been used to track employee information and accident statistics. However, no method has, prior to the present invention, interrelated predefined lists of the possible variables used in accident reporting to repeatably produce consistent accident reports, nor has any previously done so using a plurality of defined lists of such variables stored on a computer.

DISCLOSURE OF THE INVENTION

The present invention includes predefined lists of selected variables, the methods of creating and interrelating such lists, and the methods of using such lists to produce incident reports. The lists are created and modified through the use of formatted computer screens, referred to herein as input forms, and the reports are produced through the use of formatted computer outputs, referred to herein as output formats. The lists include accident-related information such as industry types, occupations, safety teams, attendance codes, types of injuries, body parts affected, types of incidents, site conditions, accident causes and safety reminders. The input forms often correspond directly to the types of lists, so that there is a form through which the list of industry types is created and/or modified, and another form through which the list of occupations is created. In addition, there are input forms that allow creation and/or modification of several lists at one time, particularly when each element in one list is directly associated with one element from another list. The output formats include agency-related formats such as the OSHA 200 report discussed above, and statistical summaries used for managerial decision making. The statistical summaries may be textual or graphical, or a combination of textual and graphical.

BRIEF DESCRIPTION OF THE DRAWINGS

FIG. 4. is an example of an OSHA 200 form produced by the present invention;

FIG. 7. is an example of a graphical accident analysis by day of the week, produced by the present invention;

FIG. 8. is an example of a textual/graphical accident analysis showing the status of accident investigations, produced by the present invention;

FIG. 9. is an example of a textual report showing the vital statistics for employees, produced by the present invention;

FIG. 10. is an example of a textual accident analysis listing a synopsis of each accident by period, produced by the present invention; and FIG. 11 is a data flow diagram of the present invention.

FIGS. 12–71 are illustrations from the operating instructions of a preferred embodiment of the invention.

DETAILED DESCRIPTION OF THE PREFERRED EMBODIMENT

Figure 1:
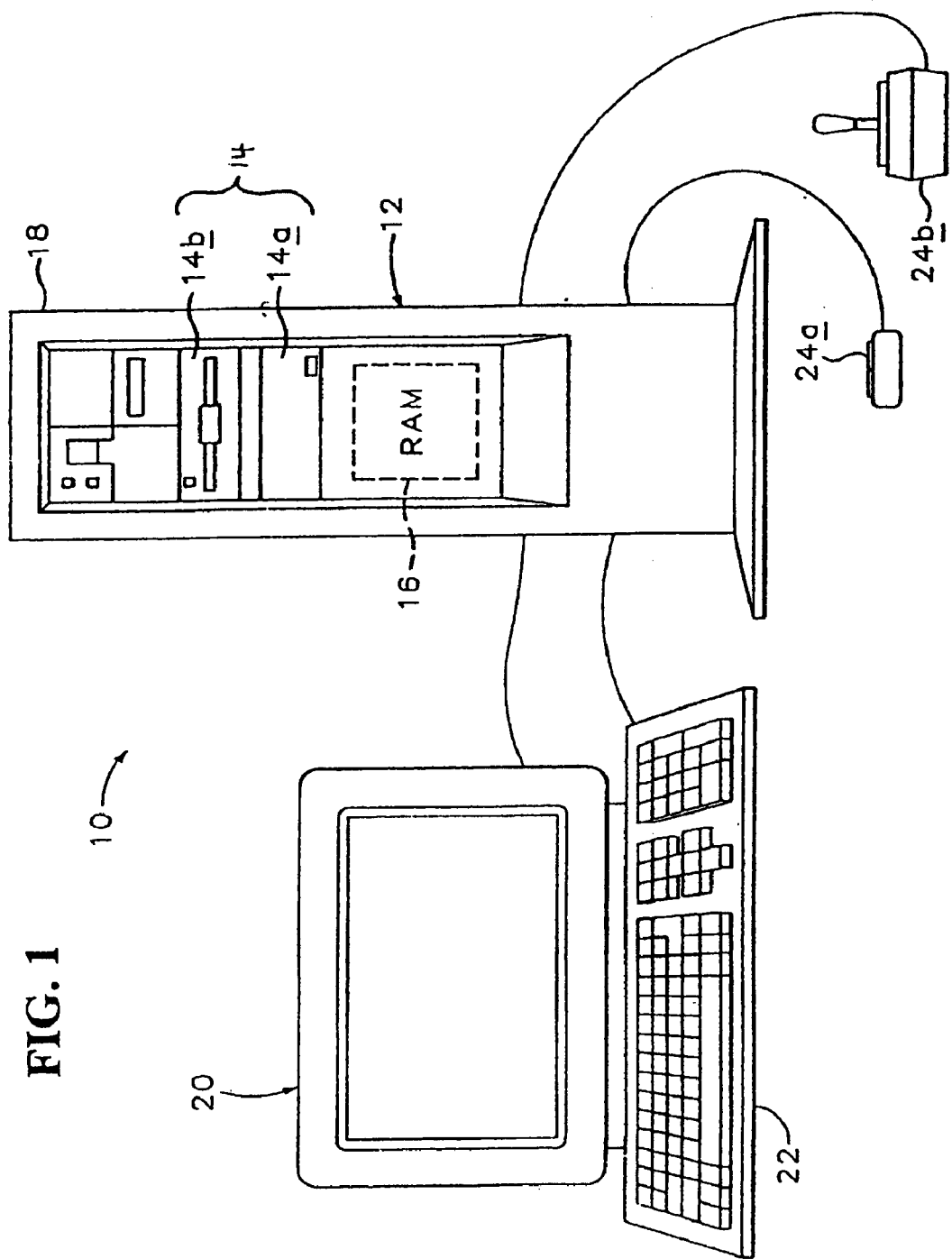
FIG. 1. is a conventional user workstation that may act as a hardware/firmware platform for the software of the present invention, including an accident reporting system and invented method and apparatus which forms a part thereof.

Referring first to FIG. 1, a user workstation is shown generally at 10, including a general-purpose computer typically providing a digital processor 12 containing an arithmetic logic unit (ALU) and various registers typically including register stacks, scratchpad memories and accumulators. Skilled persons also will appreciate that the workstation also typically will provide computer memory such as mass data storage 14, e.g. a hard or flex disk drive 14a, 14b, or both, as well as a quantity of read-and-write semiconductor memory (RAM) 16 (shown in outline as residing within workstation 10 and its housing 18) in which application programs reside for execution by processor 12. Finally, skilled persons will appreciate that the workstation also typically will provide one or more user interfaces or display mediums such as a video display terminal (VDT) 20, a keyboard 22 and an associated display cursor control system 24 including, for example, a mouse or joystick 24a, 24b, or both. In addition to disk drives 14a and b, RAM 16 and VDT 20, other computer output mediums might be included such as printers, communication networks or other storage devices. All such conventional hardware, firmware and software-executing-on-a-hardware/firmware platform architectures for the accident report system of the present invention are contemplated, and all are within the spirit and scope of the present invention.

Figure 2:
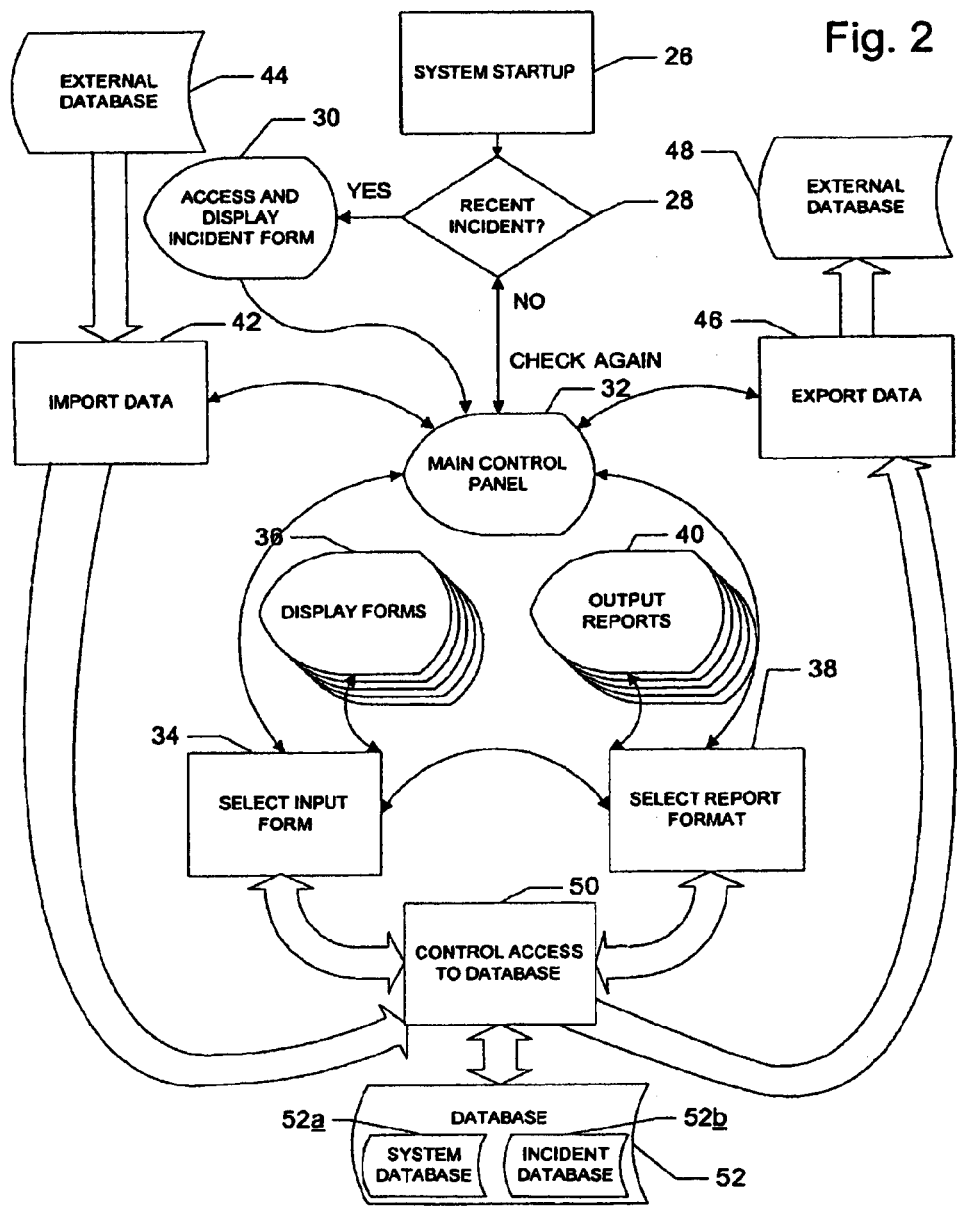
FIG. 2. is a control flow diagram of the software of the present invention.

Referring now to FIG. 2, a highly simplified control flow diagram is shown of the software executed on user workstation(s) 10 of the present system. The software is preferably stored on mass data storage device 14, then loaded into RAM 16 by digital processor 12. The represented steps of displaying control panels, forms and reports are logical displays, generated by digital processor(s) 12 on one or more VDTs 20 at one or more user workstations 10. The user would then be able to review the information on VDTs 20 and modify the database(s) stored on mass storage device(s) 14. This is done through the use of input devices like keyboards 22 or display cursor control systems 24.

A step of system startup 26 includes a verification of database integrity by determining if any other users currently are attached to the database, and to verify that all required elements of the database are available. After startup 26, there is a check to determine if any recent incidents have occurred, at 28. If such an incident has occurred, then the incident form is accessed and displayed at 30. If there is no recent incident, or if review of such a recent incident is completed, control is then transferred to the main control panel 32, another logical display operated on by the user through keyboards 22 or display cursor control systems 24.

One option at control panel 32 is to check again to determine if there are any recent incidents by returning to step 28. A second option is to direct the operation of the program to selecting an input form, at 34. Once such an input form has been selected, it is displayed at 36. When the user is done reviewing the displayed form, another input form may be selected at 34. Alternatively, there is a return to the main control panel at 32.

A third option from the main control panel is to direct control to selecting a report format, at 38. A selected report format is displayed as indicated at 40, after which control is returned to selecting a report format at 38. As with selecting an input form at 34, control can now be returned to the main control panel at 32.

Cross-transfer of control is available from selecting an input format 32 directly to selecting a report format at 38, and vice versa, as shown.

A fourth transfer available from the main control panel at 32 is to import data at 42, from external databases, at 44. Similarly, control can be transferred from the main control panel at 32 to export data at 46, to external databases, at 48.

Each of the above steps usually requires access at 50 to the internal database(s) 52. This access is controlled to ensure system data integrity and confidentiality. Database 52 is preferably stored on mass storage devices 14 that are controlled and accessed through a single digital processor 12, with the step of controlling access being performed by this processor 12. Processor 12 may in turn be connected to other user work stations 10, for example through a local area network (LAN), a wide area network (WAN) or a modem.

For reference, database 52 could include a system database containing lists of entries or records that might be selected to describe any given incident, an incident database containing lists of records that describe specific incidents, or both. The system database might also be referred to as a company database, particularly when the database has been customized for a particular company. For example, database 52 might include information on the company address, parents or subsidiaries, employees or specific types of incidents expected in the company's operations.

Figure 3:
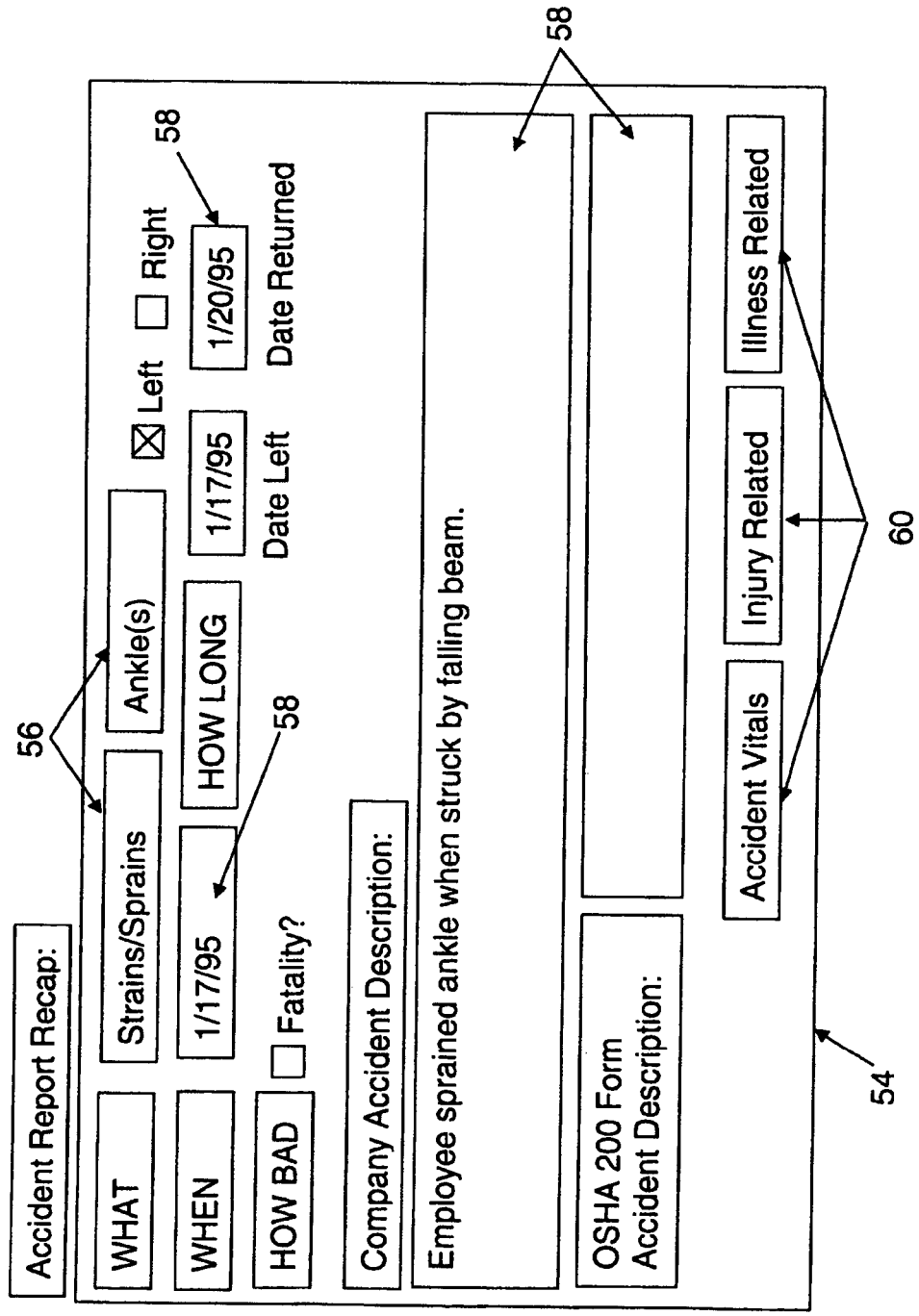
FIG. 3. is an example of a form through which information is added to a list as part of the present invention.

Referring now to FIG. 3, a sample input form is shown, including a screen image 54. Within screen image 54 there are insert-from-list fields at 56, which when selected with cursor control system 24 present a defined list of selectable variables from the system database. Cursor control 24 can then be operated to select one of such variables and to enter the selected variable into field 56. Next, there are direct-entry fields 58, into which the user inserts the requested information, using, for example, keyboard 22. Fields 56 may also provide for such direct entry of information. Screen image 54 further includes one or more control buttons 60, the selection of which, using cursor control 24, transfers control from the displayed form to a different form, report or control panel. Exiting screen image 54 causes the added or modified information from fields 56 and 58 to be written to incident database 52b.

An example of a completed OSHA 200 report is shown in FIG. 4. This report includes numerous rows 62 and columns 64 of information. The rows represent a record for a single incident, and the columns represent selected elements or entries from such records.

Figure 5:
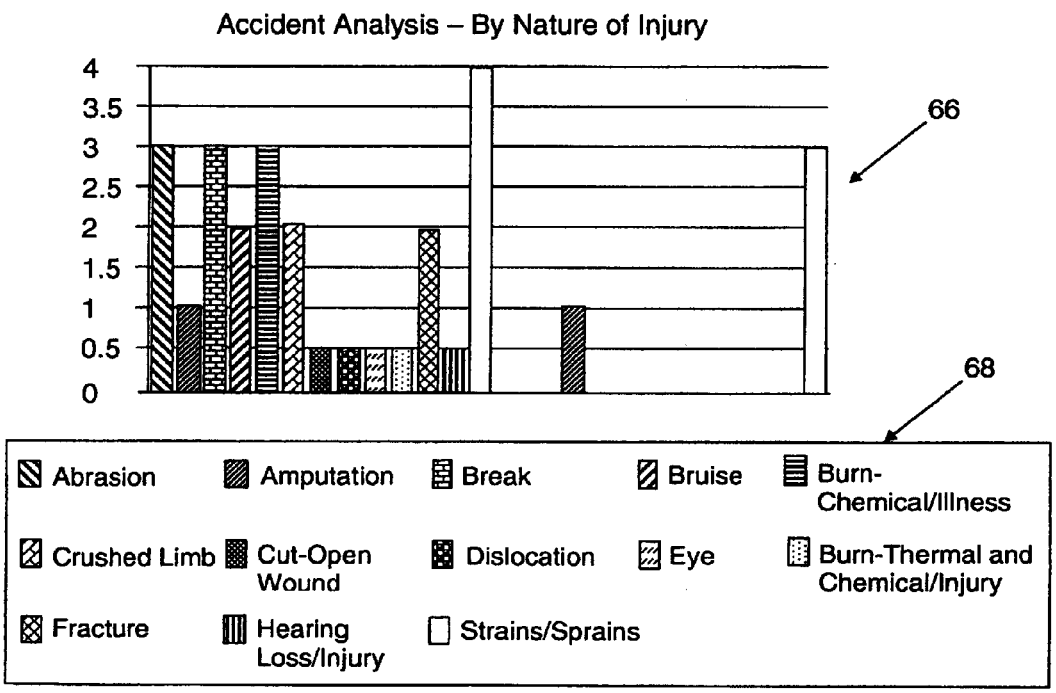
FIG. 5. is an example of a graphical accident analysis by nature of injury, produced by the present invention.
Figure 6:
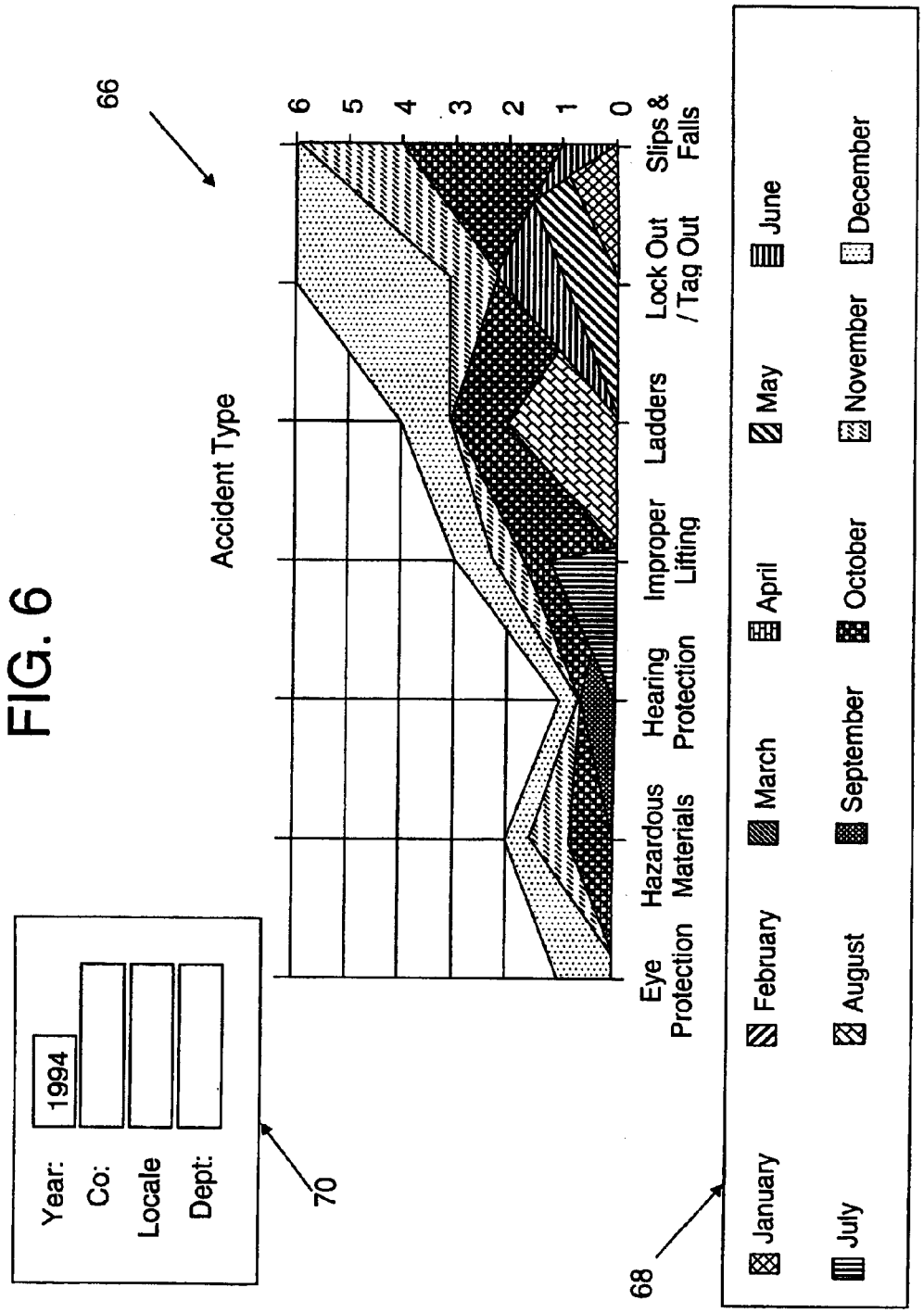
FIG. 6. is an example of a graphical accident analysis by type of accident, produced by the present invention.
Figure 15:
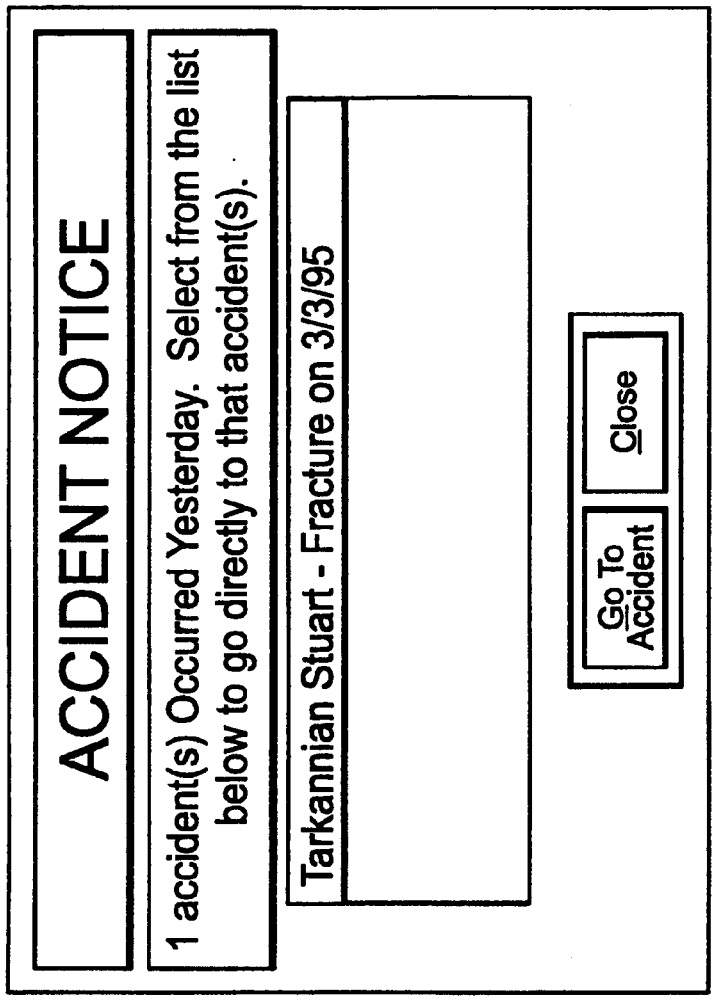
Figure 12:
Figure 13:
Figure 14:
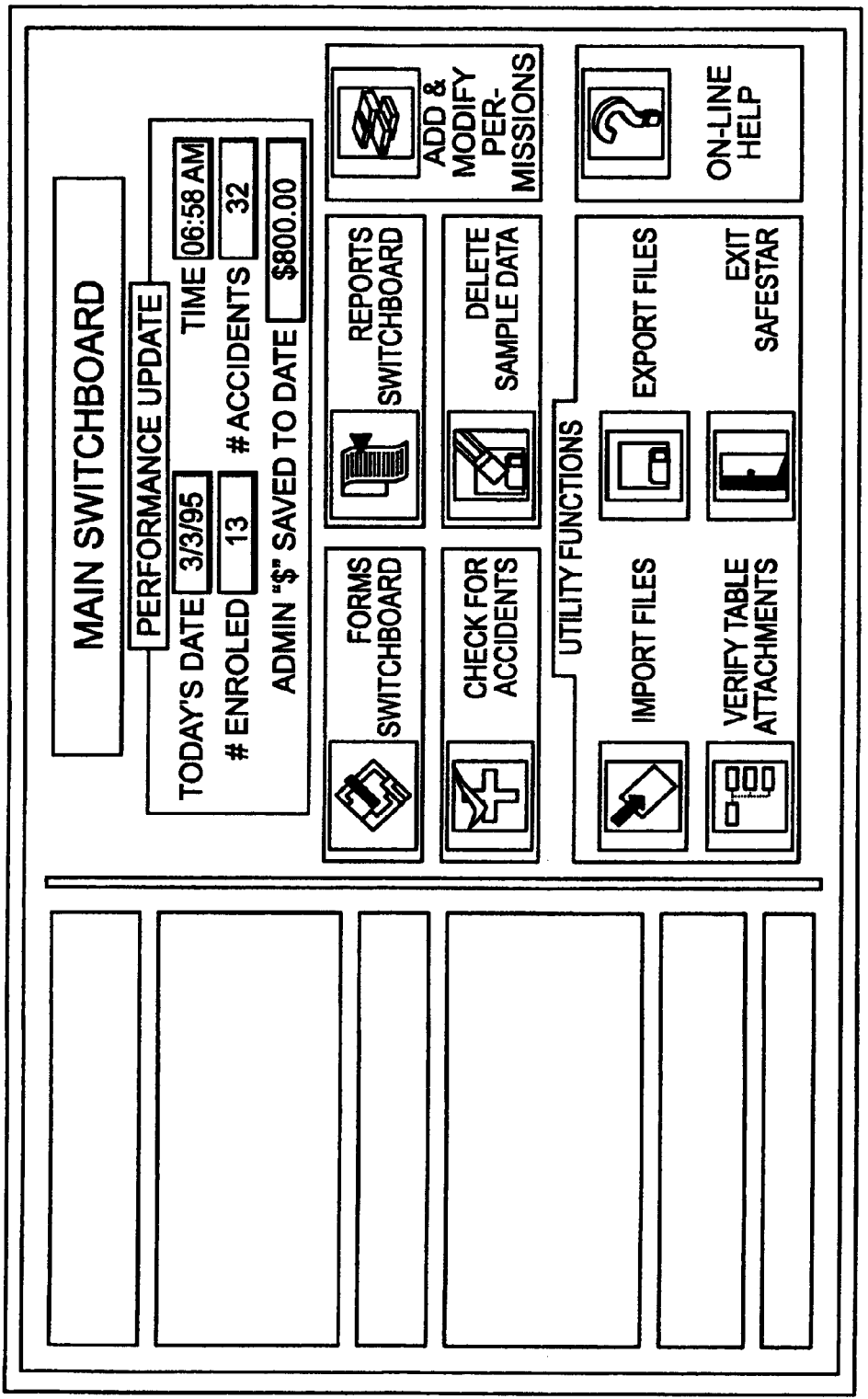
Figure 16:
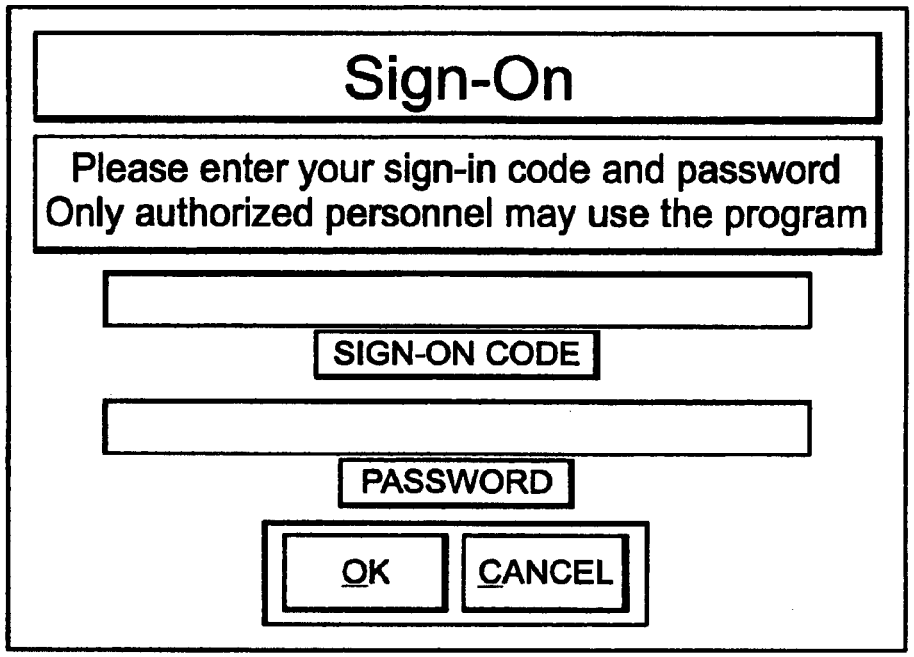
Figure 17:
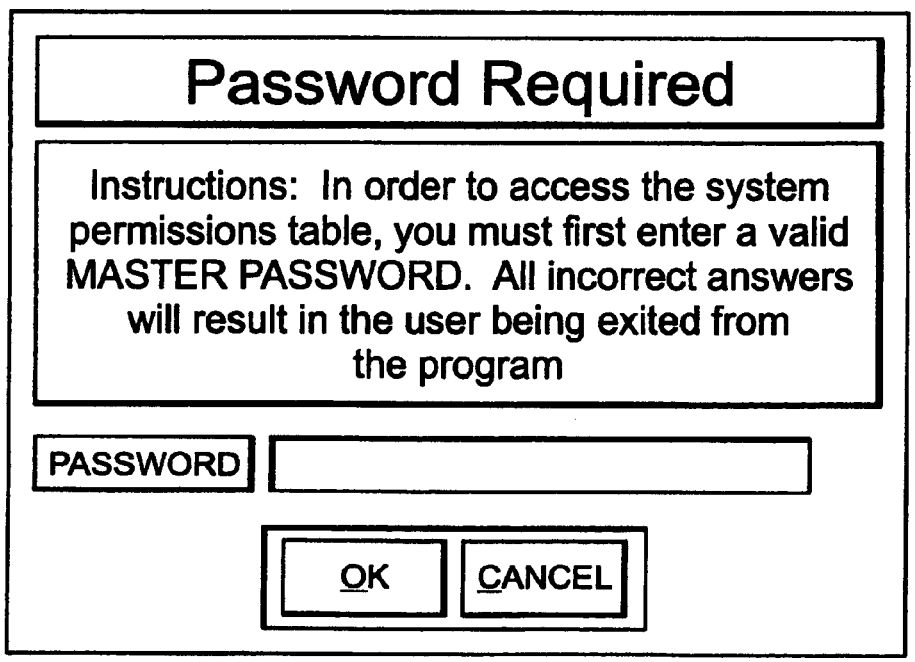
Figure 19:
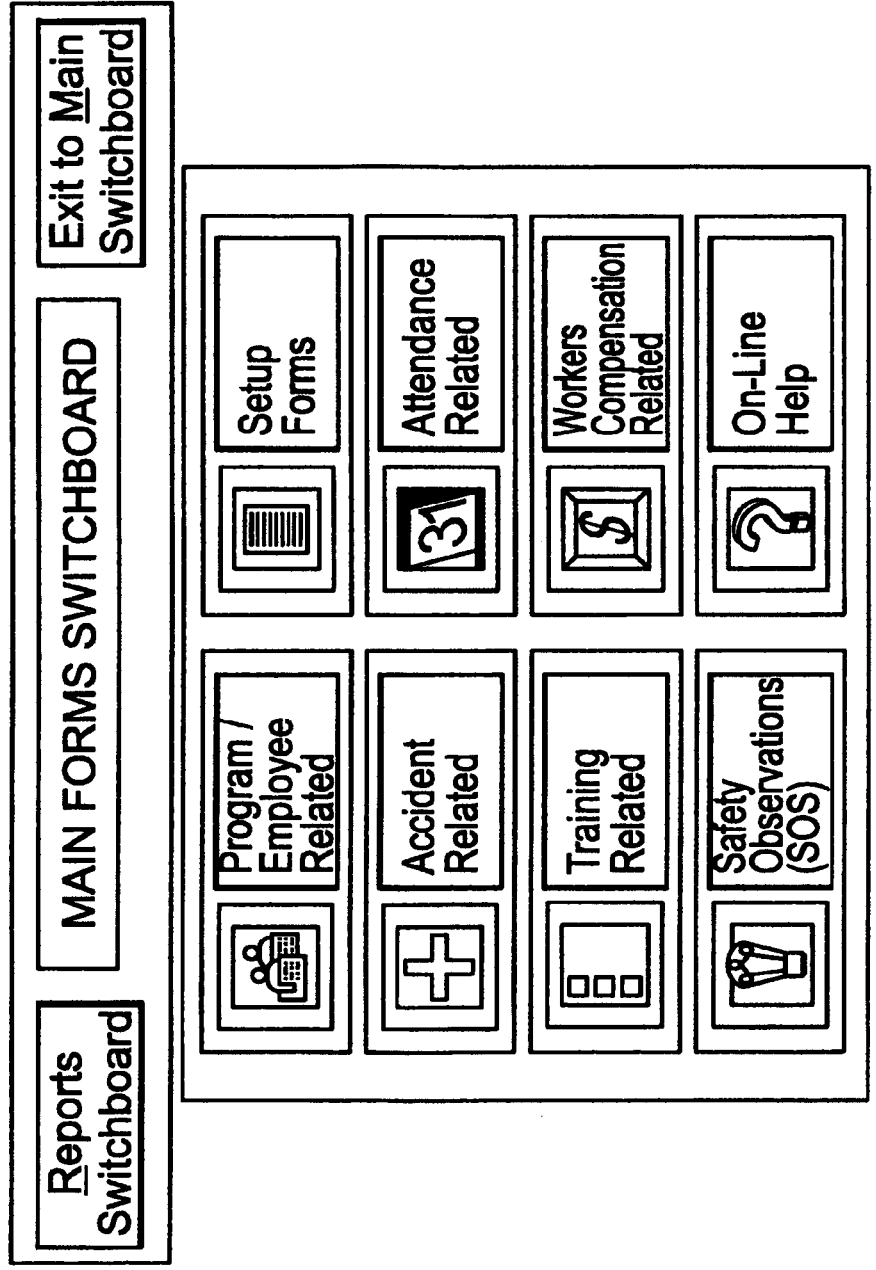
Figure 20:
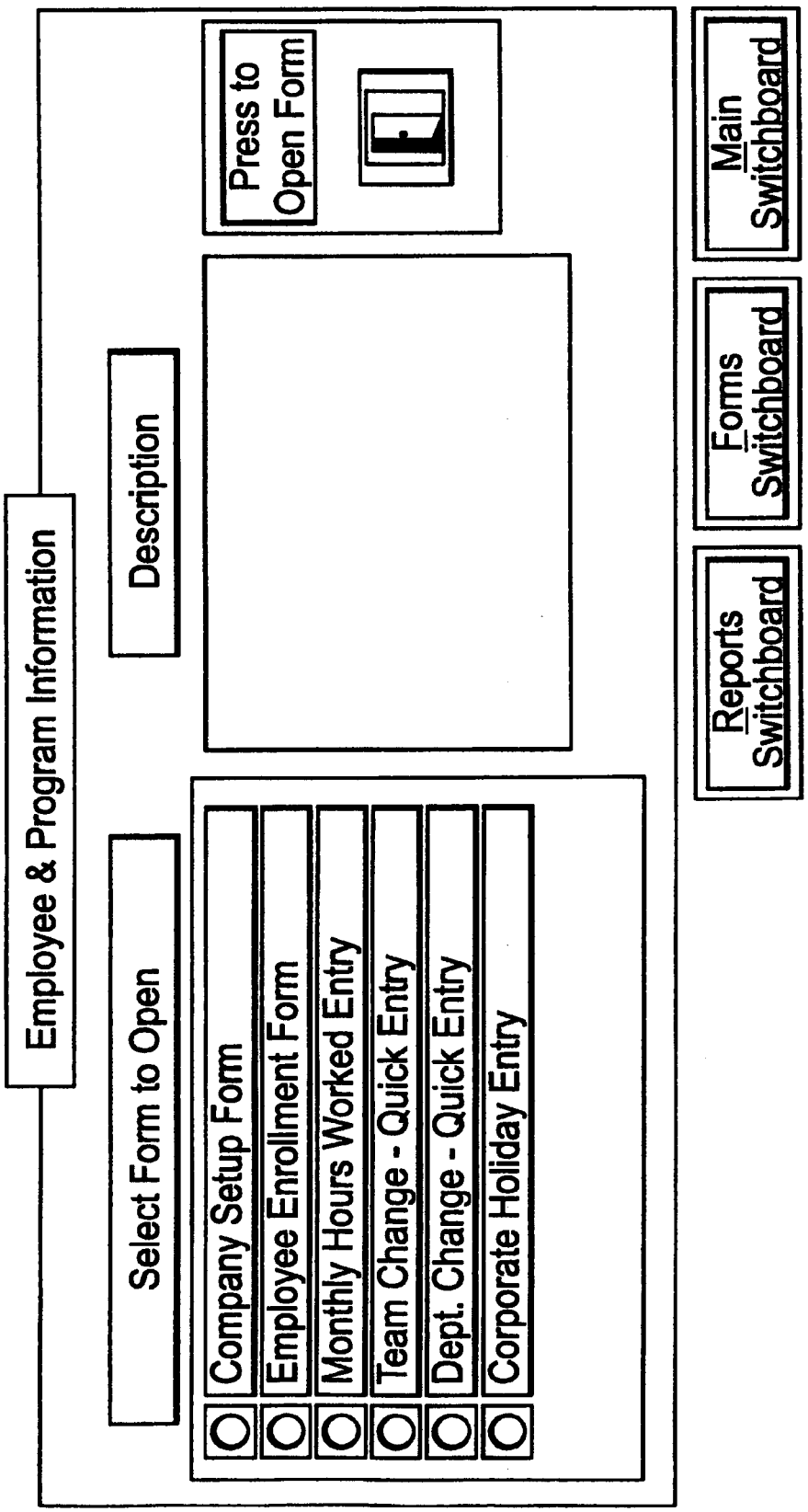
Figure 21:
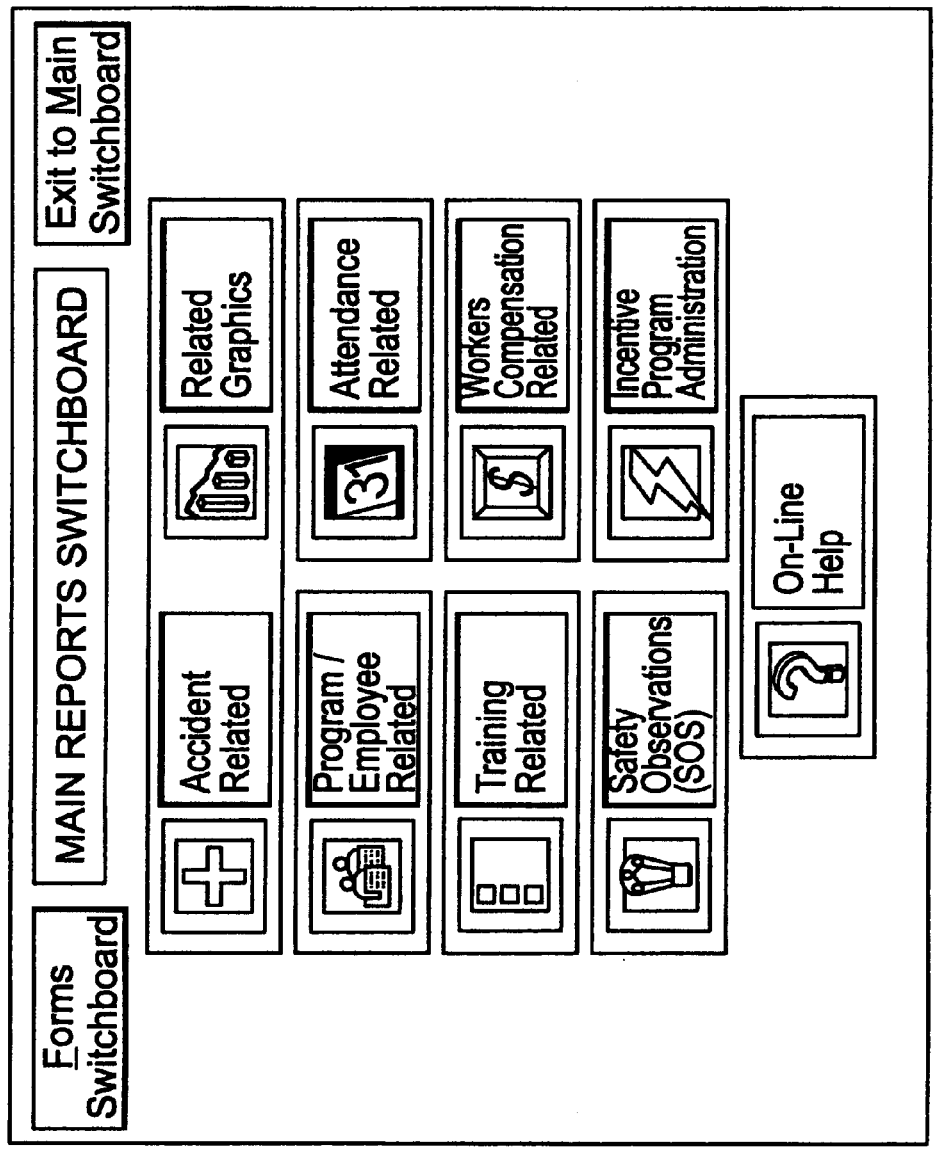
Figure 22:
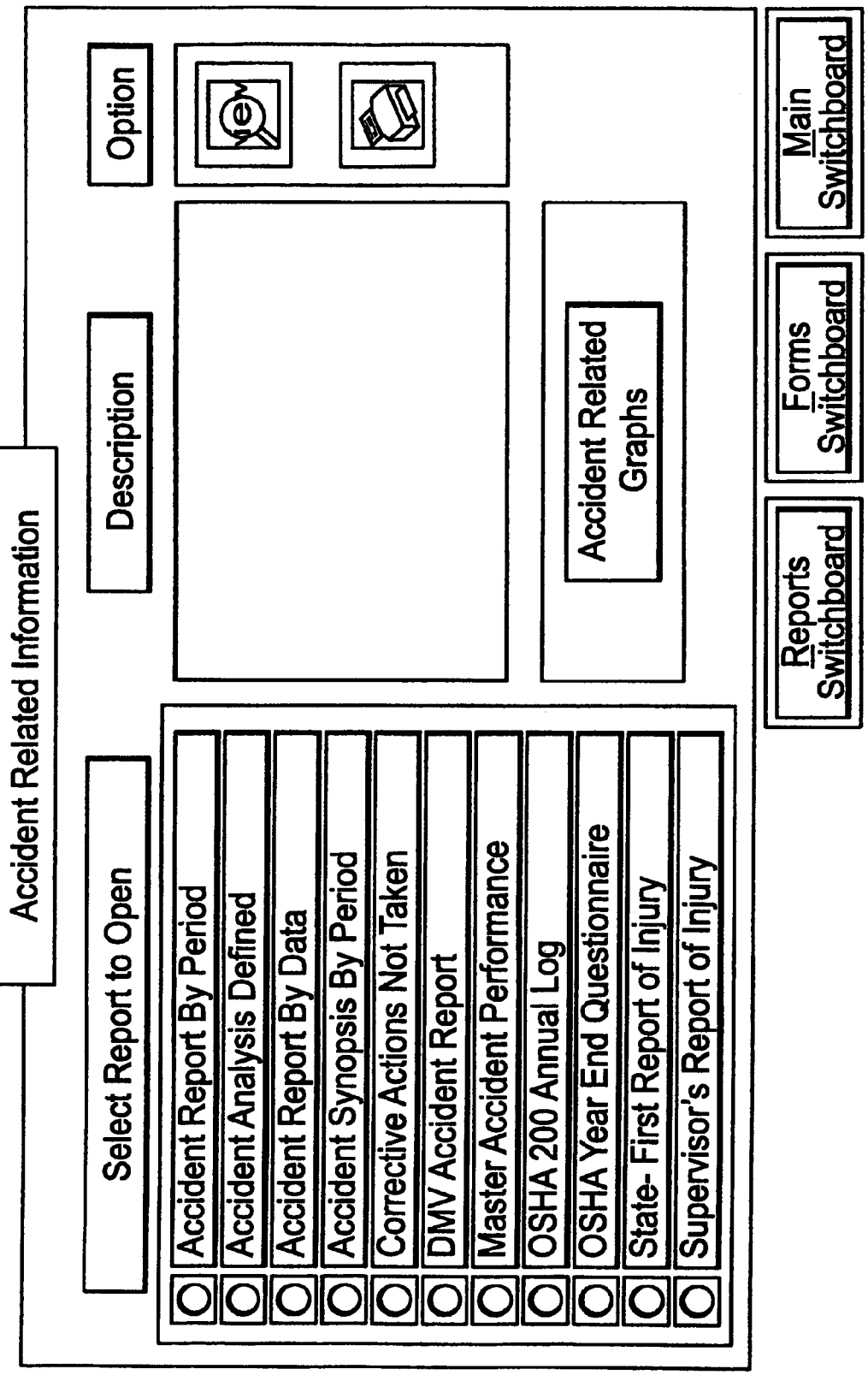
Figures 37, 38:
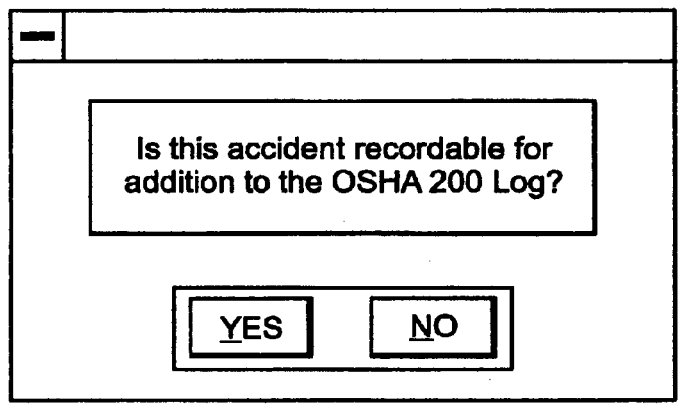
Figure 67:
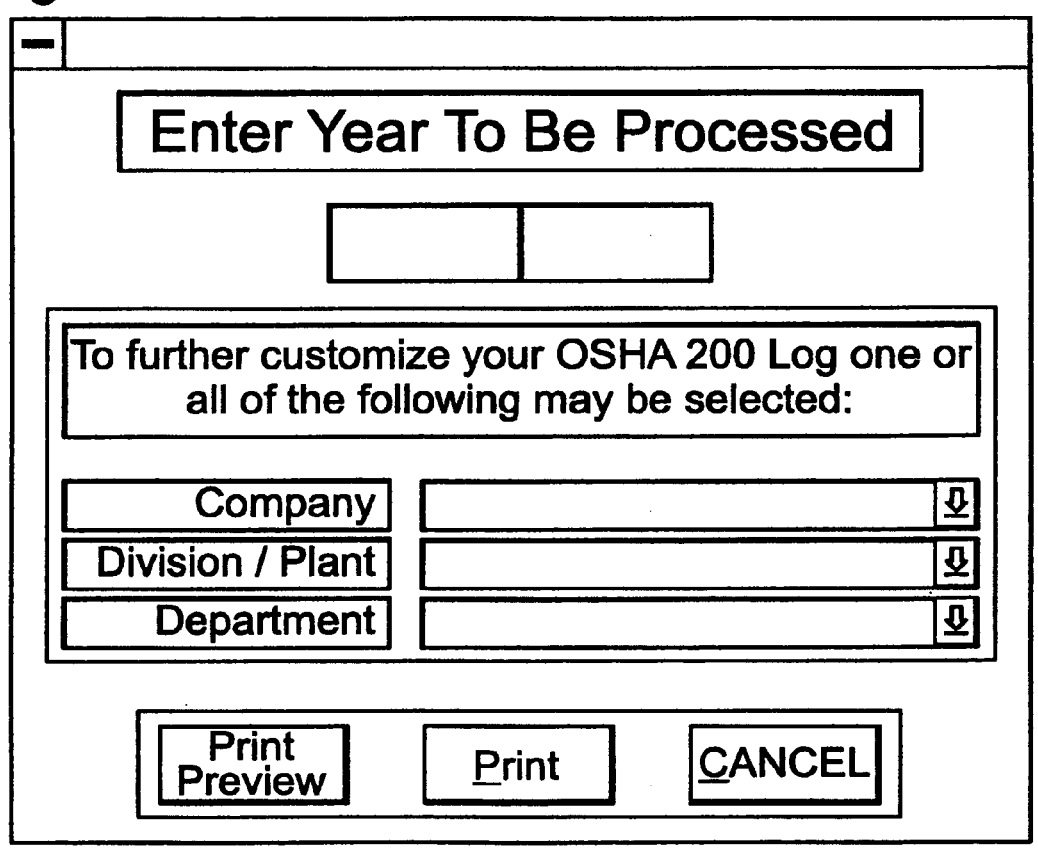
Figure 68:
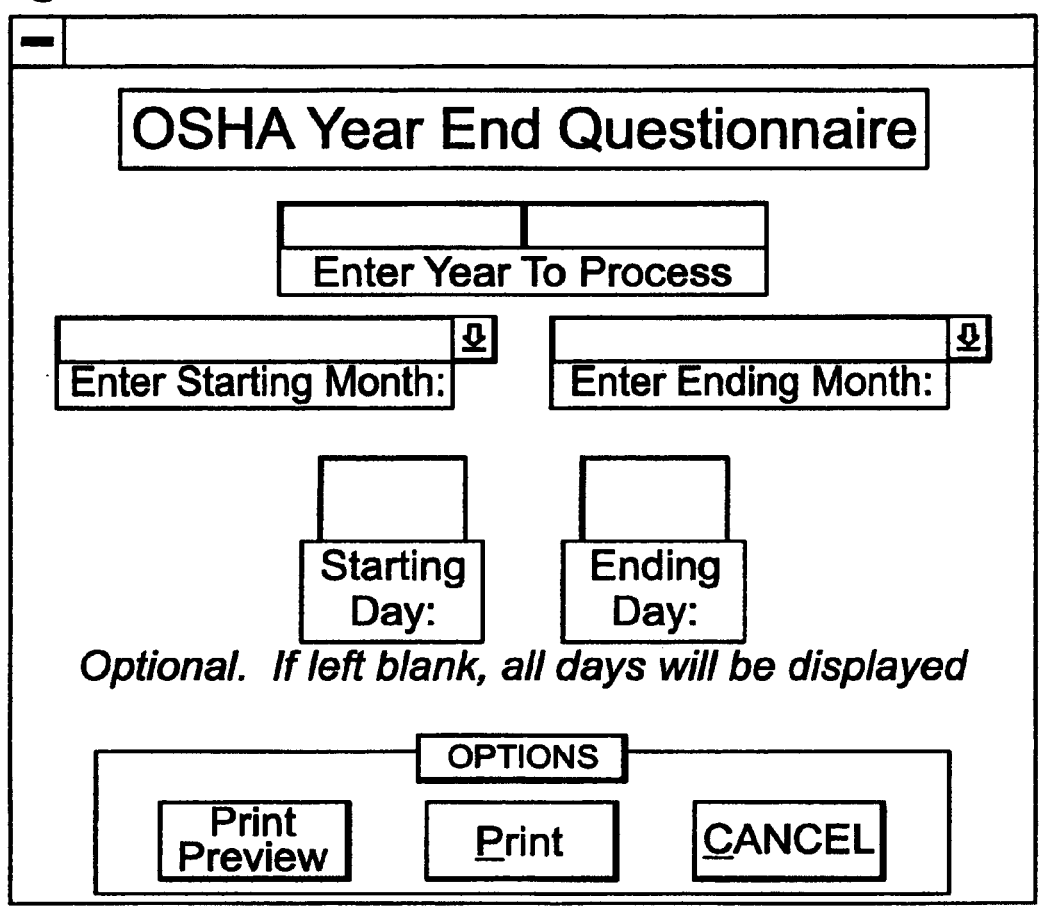
Figure 69:
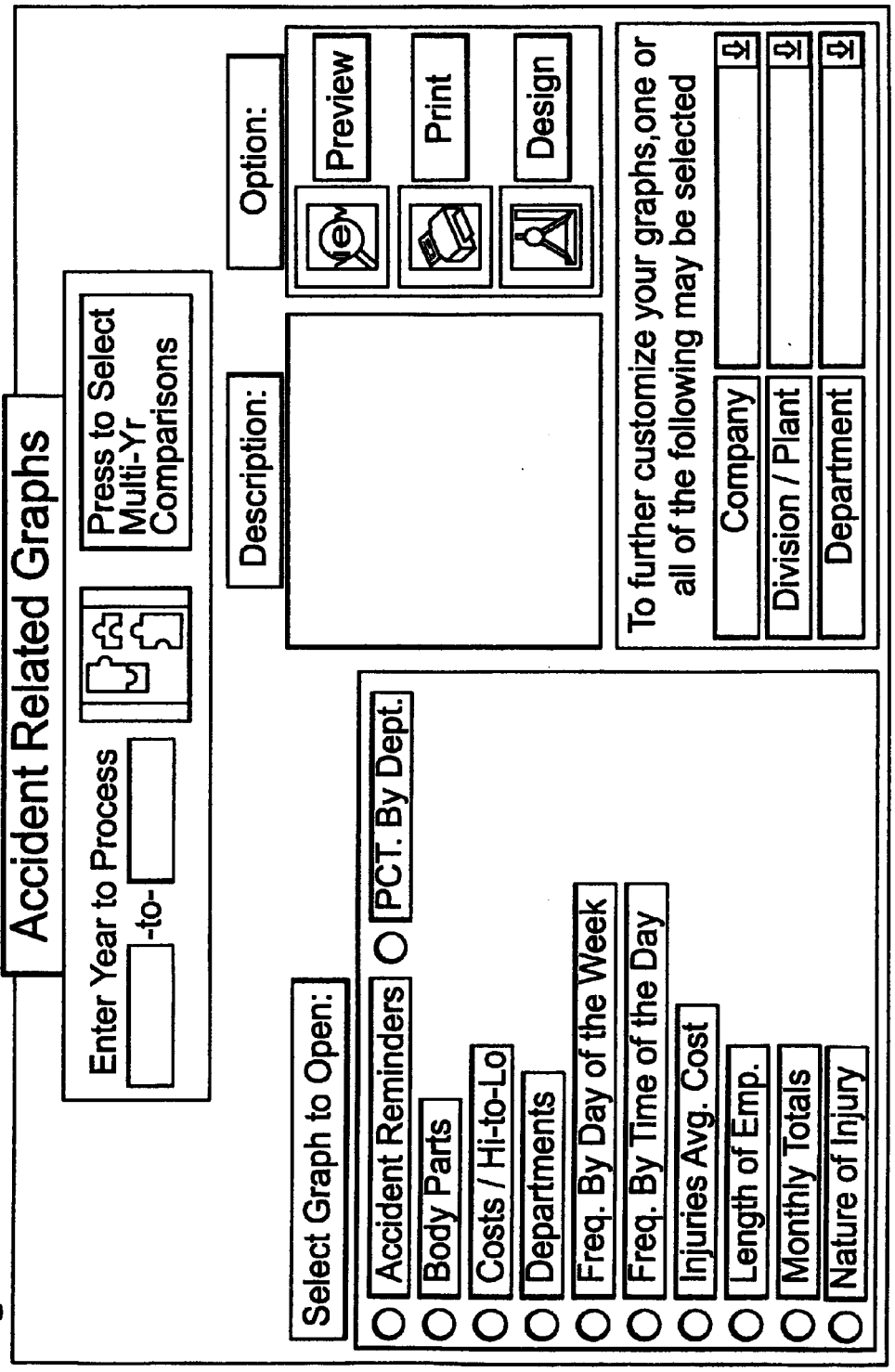
Figure 70:
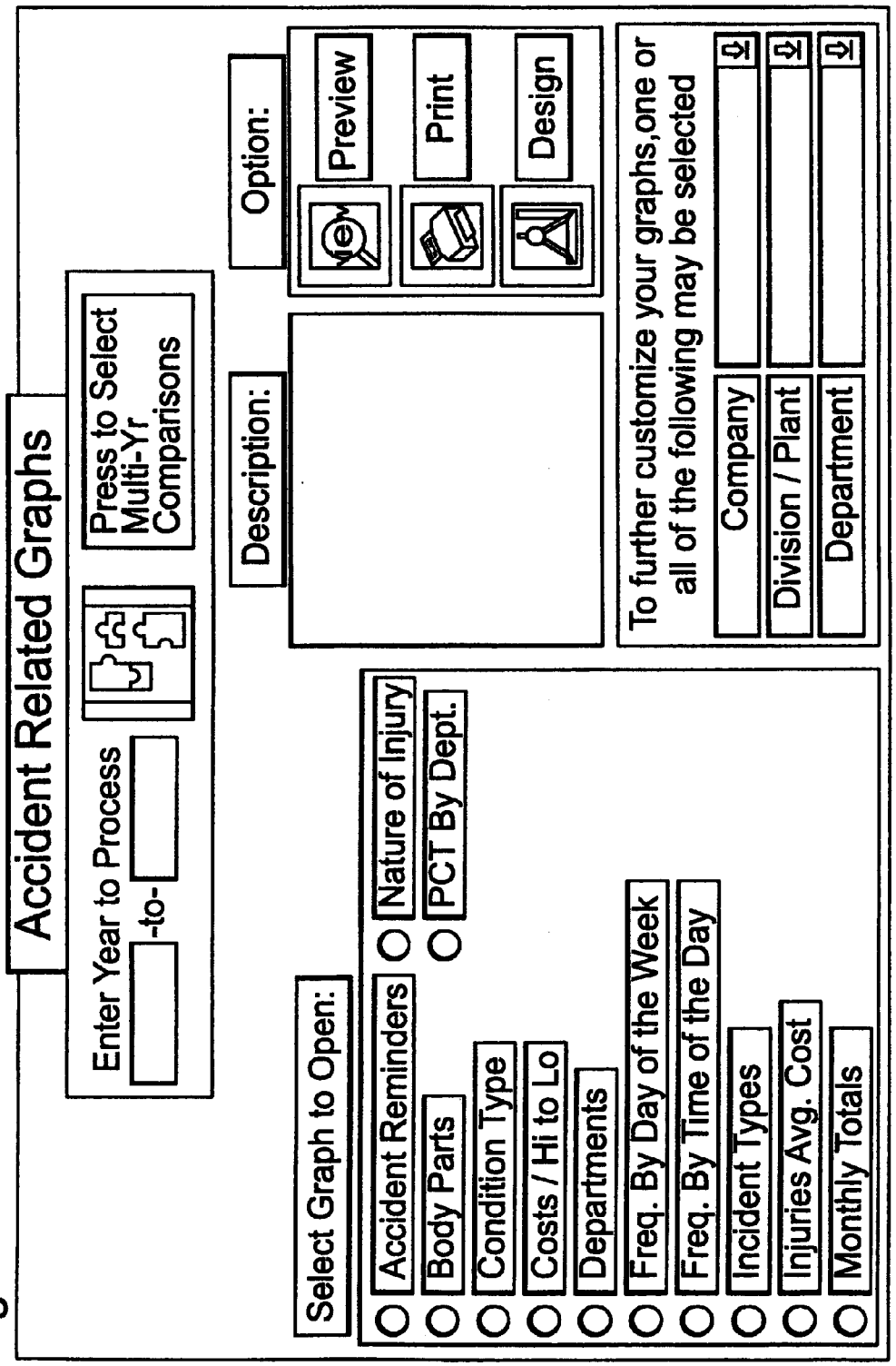

In FIGS. 5, 6 and 7, graphical reports are shown, with the graph being indicated generally at 66, a key being indicated at 68, and summary of the scope of the report being indicated at 70. In FIGS. 8, 9 and 10, textual reports are shown with text fields at 72 and with graphical status indicators at 74.

It will be appreciated that the overall database structure can be accomplished in many different forms. For example, each of the lists referred to in more detail below could be stored in a separate file in either mass data storage device 14 or RAM 16, or several or all of the lists could be accumulated into a single file in such devices. Furthermore, the files could be stored on a variety of different storage media, or even distributed about either a local area network or a wide area network. Thus, reference herein to a system database as opposed to an incident database could be reference to the same file/storage device 14/16, or an intertwined assemblage of files/storage devices 14/16, whether closely or loosely associated.

The use of "system" and "incident" identifiers for databases 52a and 52b is not as a description of a particular database structure, but as a description of the relationship of one type of list of records to another. The system database includes a plurality of defined lists of system records of selected variables and a plurality of defined report formats for producing selected incident reports. The selected variables define possible aspects of a given incident, such as the body part injured. By pre-defining the variables, completion of incident reports is standardized. For example, a human arm can also be referred to as an upper limb or an upper extremity, detailed to include the forearm, elbow and upper arm, or described using specific tissues or bones. If the list of body parts includes a record listing "ARM," then the user need only select this record, and need not deliberate as to whether the proper description would be one of the above-discussed alternatives. The selecting of a specific record also includes the automatic step of extracting the selected record from the system database for manipulation and/or use in a different record.

The incident database includes one or more defined lists of incident records of data, each incident record describing one or more aspects of a specific incident. Using the present invention, each incident record would normally contain one or more elements that were extracted and/or manipulated from the system database, as discussed above. Thus, each incident record would be standardized, regardless of who entered the information into the incident record.

The use of the system database to complete a record in the incident database also allows for the efficient creation of a more complete record. For example, when an incident occurs, all that may be known is the name of the injured worker and a simple description of what happened. By accessing the system database using that worker's name alone, additional information can be inserted automatically into the incident record, such as the worker's address, social security number, insurer, manager or special medical issues. Furthermore, the selection of a specific type of incident from a predefined list may automatically insert into the incident record a list of suggested corrective actions, follow-up procedures or reporting requirements. In addition, such selection might automatically generate a message for communication to a predefined list of other affected workers about the accident, and about how to avoid further accidents.

A further aspect of the present invention is to provide a direct comparison of the incident for which the user is viewing or modifying the information in the incident database to previously recorded incident records. For example, when a manager is inputting the initial information about an incident caused by constricted space, if there are other incidents already recorded in which constricted space was a contributing cause, the number of these similar, earlier incidents would be displayed on the incident input form. This immediate feedback is helpful in highlighting and identifying possible corrective steps to prevent the occurrence of yet further accidents.

In the preferred embodiment, the system/incident database(s) include at least the following lists of records: LIST OF DATABASES, INPUT FORMS, INPUT FORM DESCRIPTIONS, REPORT FORMATS, REPORT FORMAT DESCRIPTIONS, PARENTS/SUBSIDIARIES, COMPANY INFORMATION, INDUSTRY TYPES, LOCATIONS, OCCUPATIONS, DEPARTMENTS, SAFETY TEAMS, HOLIDAYS, EMPLOYEES, ATTENDANCE, ABSENCE CODES, HOSPITALS, ACCIDENTS, NATURE OF INJURY, BODY PARTS, INCIDENT TYPE, CONDITIONS, CAUSES, FED/STATE AGENCIES, AGENCY RECORDINGS, AWARENESS CODES, TRAINING CLASSES, TRAINING INTERVALS, TRAINING ROSTERS, TRAINING TESTS, TEST RESULTS and SAFETY REMINDERS.

The preferred data record structure of some of the lists of the system database are demonstrated by tables 1–3.

TABLE 1

List of Fields For Import/Export Purposes-Company Setup

| # | Field Name | Description | Data Type |
|---|---|---|---|
| 1. | Company Name | Company Name | Text |
| 2. | Address #1 | Address 1 of Company | Text |
| 3. | Address #2 | Address 2 of Company | Text |
| 4. | City | Company City | Text |
| 5. | State | Company State | Text |
| 6. | Zip | Company Zip | Text |
| 7. | County | Company County | Text |
| 8. | Phone | Company Phone | Text |
| 9. | Fed ID Number | Employer's FEIN | Number |
| 10. | Plant/Location # | Company's Plant and Location No. | Text |
| 11. | Primary Contact | Primary Contact w/ Company | Text |
| 12. | Secondary Contact | Second Company Contact | Text |
| 13. | General Mgr or President | General Manager or President of Co. | Text |
| 14. | General Nature of Business | General Nature of Business | Text |
| 15. | Primary Hospital | Primary-Use Hospital for Co. | Text |
| 16. | # Accidents To-Date | No. of Accidents To-Date | Number |
| 17. | # Employees Enrolled To-Date | No. of Employees Enrolled To-Date | Number |
| 18. | Avg Length of Employment | Average Length of Employment | Number |
| 19. | State of Operation | State of Operation | Text |
| 20. | Corp Type-Corporation | CB/Corporation Type of Corporation | Yes/No |
| 21. | Corp Type-Partnership | CB/Partnership Type of Corporation | Yes/No |
| 22. | Corp Type-Other | CB/Other Type of Corporation | Yes/No |
| 23. | Ins Co | Insurance Co. Name | Text |
| 24. | Ins Address1 | Insurance Co. Address1 | Text |
| 25. | Ins Address2 | Insurance Co. Address2 | Text |
| 26. | Ins City | Insurance Co. City | Text |
| 27. | Ins State | Insurance Co. State | Text |
| 28. | Ins Zip | Insurance Co. Zip | Text |
| 29. | Ins Phono | Insurance Co. Phone | Text |
| 30. | Ins Division1 | Insurance Co. Division1 | Text |
| 31. | Ins Division2 | Insurance Co. Division2 | Text |
| 32. | Ins Division3 | Insurance Co. Division3 | Text |
| 33. | Co Logo | Company's Logo | OLE Object |

Note: The file you are importing must include all of the above listed columns in the order and data types. If your file does not originally have all of these fields (which it probably won't), you will need to make a "SPACER" column for each one that is missing and insert them in the correct position.
This "SPACER" function will be much easier if you are importing a spreadsheet file, than if you are importing an ASCII text file. Remember, even if your file is an ASCII text file, you can open that text file in Excel or Lotus and use the "Parse" function to separate the information into organized columns. Then import the completed files.

TABLE 2

List of Fields For Import/Export Purposes-Master Names

| # | Field Name | Description | Data Type |
|---|---|---|---|
| 1. | ID | Employee ID | Counter |
| 2. | LAST | Employee's Last Name | Text |
| 3. | FIRST | Employee's First Name | Text |
| 4. | SSN | Employee's Social Security Number | Number |
| 5. | Birthday | Employee's Date of Birth | Date/Time |
| 6. | LOE | Employee's Length of Employment | Text |
| 7. | ADJ | Employee's ADJ | Date/Time |
| 8. | Address | Employee's Address | Text |
| 9. | City | Employee's City | Text |
| 10. | State | Employee's State | Text |
| 11. | Zip | Employee's Zip | Number |
| 12. | PHONE | Employee's Phone | Text |
| 13. | DEPT | Employee's Department No. | Text |
| 14. | Dept Name | Employee's Dept Name | Text |
| 15. | Company | Company Name | Text |
| 16. | Locale | Location of Company | Text |
| 17. | HrlyRate | Employee Hourly Wage | Number |
| 18. | Occupation | Employee's Occupation | Text |
| 19. | TeamCode | Employee's Team Code | Text |
| 20. | TeamName | Employee's Teamt Name | Text |

Note: The file you are importing must include all of the above listed columns in the order and data types. If your file does not originally have all of these fields (which it probably won't), you will need to make a "SPACER" column for each one that is missing and insert them in the correct position.
This "SPACER" function will be much easier if you are importing a spreadsheet file, than if you are importing an ASCII text file. Remember, even if your file is an ASCII text file, you can open that text file in Excel or Lotus and use the "Parse" function to separate the information into organized columns. Then import the completed files.

TABLE 3

List of Fields For Import/Export Purposes-Injury Reminder

| # | Field Name | Description | Data Type |
|---|---|---|---|
| 1. | Accident Type | Type of Accident | Text |
| 2. | Reminder | Reminder of Accident | Memo |

Note: The file you are importing must include all of the above listed columns in the order and data types. If your file does not originally have all of these fields (which it probably won't), you will need to make a "SPACER" column for each one that is missing and insert them in the correct position.
This "SPACER" function will be much easier if you are importing a spreadsheet file, than if you are importing an ASCII text file. Remember, even if your file is an ASCII text file, you can open that text file in Excel or Lotus and use the "Parse" function to separate the information into organized columns. Then import the completed files.

The preferred data record structures of some of the lists of the incident database are demonstrated by tables 4–6.

TABLE 4

List of Fields For Import/Export Purposes-Accident-Form

| # | Field Name | Description | Data Type |
|---|---|---|---|
| 1. | ID | Accident ID | Counter |
| 2. | Last | Employee Last Name | Text |
| 3. | First | Employee First Name | Text |
| 4. | Company | Company Name | Text |
| 5. | Locale | Co. Plant Location | Text |
| 6. | Department | Department Number | Text |
| 7. | Dept Name | Department Name | Text |
| 8. | Phone | Employee Phone Number | Text |
| 9. | DOB | Employee Date of Birth | Text |
| 10. | Sex Male | Check Box/Employee's Sex-Male | Yes/No |
| 11. | Sex Female | Check Box/Employee's Sex-Female | Yes/No |
| 12. | SSN | Employee Social Security Number | Text |
| 13. | Address | Employee Address | Text |
| 14. | City | Employee City | Text |
| 15. | State | Employee State | Text |
| 16. | Zip | Employee Zip | Number |
| 17. | LOE | Employee Length of Employment | Text |
| 18. | Hired | Date Employee Hired | Text |
| 19. | Hospitalized | Check Box/Was Employee Hospitalized | Yes/No |
| 20. | Hospital Name | Name of Hospital Emp. was taken to | Text |
| 21. | Date of Injury | Date Injury Occurred | Date/Time |
| 22. | Time of Injury | Time Injury Occurred | Date/Time |
| 23. | Time in Dept | Time Employee's been in Dept | Text |
| 24. | Name of Physician | Emp. Treating Physician | Text |
| 25. | Body Part | Part of Employee Body that was Injured | Text |
| 26. | Body Part-Left | Check Box/Left side of Emp. Body | Yes/No |
| 27. | Body Part-Right | Check Box/Right side of Emp. Body | Yes/No |
| 28. | Injured Previously | CB/Had Emp. Injured Body Part Before | Yes/No |
| 29. | Nature of Injury | Nature of Employee's Injury | Text |
| 30. | Cause | Cause of Employee's Injury | Text |
| 31. | Condition | Condition that Contributed to Injury | Text |

TABLE 4-continued

List of Fields For Import/Export Purposes-Accident-Form

| # | Field Name | Description | Data Type |
|---|---|---|---|
| 32. | Accident Type | What Type of Accident Caused Injury | Text |
| 33. | Accident Description | Description of the Accident | Memo |
| 34. | Corrective Action Taken | What Corrective Action Taken | Memo |
| 35. | Date Corrective Action Taken | Date the Corrective Action was Taken | Date/Time |
| 36. | Witness | Witness of the Accident | Text |
| 37. | Date Company Knew | Date that Company First Knew of Acc. | Date/Time |
| 38. | Street Address of Accident | Address Where Accident Occurred | Text |
| 39. | Nature of Business | Nature of Business | Text |
| 40. | County of Injury | County where Injury Occurred | Text |
| 41. | Emp Worker Status-Yes | Check Box- | Yes/No |
| 42. | Emp Worker Status-No | Check Box- | Yes/No |
| 43. | Emp Occupation | Occupation of Employee | Text |
| 44. | Length of Employment | Length of Time Emp. Worked for Co. | Date/Time |
| 45. | Injured on Premises-Yes | CB/Was Emp Injured on Premises-Yes | Yes/No |
| 46. | Injured on Premises-No | CB/Was Emp Injured on Premises-No | Yes/No |
| 47. | Fatality | CB/Was Accident a Fatality | Yes/No |
| 48. | Injured on Job-Yes | CB/Did Injury Occur on the Job-Yes | Yes/No |
| 49. | Injured on Job-No | CB/Did Injury Occur on the Job-No | Yes/No |
| 50. | Injured on Job-Unknown | CB/Injury Occur on the Job-Unknown | Yes/No |
| 51. | Other Workers Injured | CB/Were Other Workers Injured | Yes/No |
| 52. | Accident Result of Machine Failure | CB/Acc. a Result of Machine Failure | Yes/No |
| 53. | Accident Caused by Someone Else | CB/Acc. Caused by Someone Else | Yes/No |
| 54. | Company Accident Description | Company's Description of Accident | Memo |
| 55. | 801 OSHA To Be Filed? | CB/Is 801 OSHA to be Filed | Yes/No |
| 56. | Previous Injury Description | Description of Previous Injury | Text |
| 57. | Shift Start | Beginning of Employee's Shift | Date/Time |
| 58. | Shift End | End of Employee's Shift | Date/Time |
| 59. | Date Worker Left | Date Employee Left Work | Date/Time |
| 60. | Time Worker Left | Time Employee Left Work | Date/Time |
| 61. | Date Worker Returned | Date Worker Returned From Disability | Date/Time |
| 62. | Number Hrs Per Shift | Number Hrs Employee Works Per Shift | Number |
| 63. | Days Worked-3 or less | CB/Emp. Reg. Works less then 3 days | Yes/No |
| 64. | Days Worked-4 | CB/Emp. Reg. Works 4 days | Yes/No |
| 65. | Days Worked-5 | CB/Emp. Reg. Works 5 days | Yes/No |
| 66. | Days Worked-6 | CB/Emp. Reg. Works 6 days | Yes/No |
| 67. | Days Worked-7 | CB/Emp. Reg. Works 7 days | Yes/No |
| 68. | Days Off-Sat | CB/Emp. Reg. Days Off-Sat | Yes/No |
| 69. | Days Off-Sun | CB/Emp. Reg. Days Off-Sun | Yes/No |
| 70. | Days Off-Mon | CB/Emp. Reg. Days Off-Mon | Yes/No |
| 71. | Days Off-Tue | CB/Emp. Reg. Days Off-Tue | Yes/No |
| 72. | Days Off-Wed | CB/Emp. Reg. Days Off-Wed | Yes/No |
| 73. | Days Off-Thurs | CB/Emp. Reg. Days Off-Thurs | Yes/No |
| 74. | Days Off-Fri | CB/Emp. Reg. Days Off-Fri | Yes/No |
| 75. | Wage | Employee's Current Wage | Number |
| 76. | Wage-Hr | CB/Emp. Wage Per Hour | Yes/No |
| 77. | Wage-Wk | CB/Emp. Wage Per Week | Yes/No |
| 78. | Wage-Day | CB/Emp. Wage Per Day | Yes/No |
| 79. | Wage-Mo | CB/Emp. Wage Per Month | Yes/No |
| 80. | Wage-Yr | CB/Emp. Wage Per Year | Yes/No |
| 81. | DirectMedical | Direct Medical Costs to Company | Currency |
| 82. | AdminCosts | Administration Costs to Company | Currency |
| 83. | EmpCompCosts | Employer Contribution | Currency |
| 84. | TotalCompCosts | Total Compensation Costs By Company | Currency |
| 85. | EstLongTermCosts | Estimated Long Term Costs to Company | Currency |
| 86. | TeamCode | Team Code | Text |
| 87. | TeamName | Team Name | Text |

Note: The file you are importing must include all of the above listed columns in the order and data types. If your file does not originally have all of these fields (which it probably won't), you will need to make a "SPACER" column for each one that is missing and insert them in the correct position. This "SPACER" function will be much easier if you are importing a spreadsheet file, than if you are importing an ASCII text file. Remember, even if your file is an ASCII text file, you can open that text file in Excel or Lotus and use the "Parse" function to separate the information into organized columns. Then import the completed files.

TABLE 5

List of Fields For Import/Export Purposes-OSHA-AccExport

| # | Field Name | Description | Data Type |
|---|---|---|---|
| 1. | Last | Employee Last Name | Text |
| 2. | First | Employee First Name | Text |
| 3. | Name | Employee Name | Text |

TABLE 5-continued

List of Fields For Import/Export Purposes-OSHA-AccExport

| # | Field Name | Description | Data Type |
|---|---|---|---|
| 4. | ID | Accident ID | Counter |
| 5. | Department | Department Number | Text |
| 6. | Dept Name | Department Name | Text |
| 7. | Phone | Employee Phone Number | Text |
| 8. | DOB | Employee Date of Birth | Text |
| 9. | Sex Male | Check Box/Employee's Sex-Male | Yes/No |
| 10. | Sex Female | Check Box/Employee's Sex-Female | Yes/No |
| 11. | SSN | Employee Social Security Number | Text |
| 12. | Address | Employee Address | Text |
| 13. | City | Employee City | Text |
| 14. | State | Employee State | Text |
| 15. | Zip | Employee Zip | Number |
| 16. | LOE | Employee Length of Employment | Text |
| 17. | Hired | Date Employee Hired | Text |
| 18. | Hospitalized | Check Box/Was Employee Hospitalized | Yes/No |
| 19. | Hospital Name | Name of Hospital Emp. was taken to | Text |
| 20. | Date of Injury | Date Injury Occurred | Date/Time |
| 21. | Month | Month | Text |
| 22. | Time of Injury | Time Injury Occurred | Date/Time |
| 23. | Time in Dept | Time Employee's been in Dept | Text |
| 24. | Name of Physician | Emp. Treating Physician | Text |
| 25. | Body Part | Part of Employee Body that was Injured | Text |
| 26. | Body Part-Left | Check Box/Left side of Emp. Body | Yes/No |
| 27. | Body Part-Right | Check Box/Right side of Emp. Body | Yes/No |
| 28. | Injured Previously | CB/Had Emp. Injured Body Part Before | Yes/No |
| 29. | Nature of Injury | Nature of Employee's Injury | Text |
| 30. | Cause | Cause of Employee's Injury | Text |
| 31. | Condition | Condition that Contributed to Injury | Text |
| 32. | Accident Type | What Type of Accident Caused Injury | Text |
| 33. | Accident Description | Description of the Accident | Memo |
| 34. | Corrective Action Taken | What Corrective Action Taken | Memo |
| 35. | Date Corrective Action Taken | Date the Corrective Action was Taken | Date/Time |
| 36. | Witness | Witness of the Accident | Text |
| 37. | Date Company Knew | Date that Company First Knew of Acc. | Date/Time |
| 38. | Street Address of Accident | Address Where Accident Occurred | Text |
| 39. | Nature of Business | Nature of Business | Text |
| 40. | County of Injury | County where Injury Occurred | Text |
| 41. | Emp Worker Status-Yes | Check Box- | Yes/No |
| 42. | Emp Worker Status-No | Check Box- | Yes/No |
| 43. | Emp Occupation | Occupation of Employee | Text |
| 44. | Length of Employment | Length of Time Emp. Worked for Co. | Date/Time |
| 45. | Injured on Premises-Yes | CB/Was Emp Injured on Premises-Yes | Yes/No |
| 46. | Injured on Premises-No | CB/Was Emp Injured on Premises-No | Yes/No |
| 47. | Fatality | CB/Was Accident a Fatality | Yes/No |
| 48. | Injured on Job-Yes | CB/Did Injury Occur on the Job-Yes | Yes/No |
| 49. | Injured on Job-No | CB/Did Injury Occur on the Job-No | Yes/No |
| 50. | Injured on Job-Unknown | CB/Injury Occur on the Job-Unknown | Yes/No |
| 51. | Other Workers Injured | CB/Were Other Workers Injured | Yes/No |
| 52. | Accident Result of Machine Failure | CB/Acc. a Result of Machine Failure | Yes/No |
| 53. | Accident Caused by Someone Else | CB/Acc. Caused by Someone Else | Yes/No |
| 54. | Company Accident Description | Company's Description of Accident | Memo |
| 55. | 801 OSHA To Be Filed? | CB/Is 801 OSHA to be Filed | Yes/No |
| 56. | Previous Injury Description | Description of Previous Injury | Text |
| 57. | Shift Start | Beginning of Employee's Shift | Date/Time |
| 58. | Shift End | End of Employees Shift | Date/Time |
| 59. | Date Worker Left | Date Employee Left Work | Date/Time |
| 60. | Time Worker Left | Time Employee Left Work | Date/Time |
| 61. | Date Worker Returned | Date Worker Returned From Disability | Date/Time |
| 62. | Number Hrs Per Shift | Number Hrs Employee Works Per Shift | Number |
| 63. | Days Worked-3 or less | CB/Emp. Reg. Works less then 3 days | Yes/No |
| 64. | Days Worked-4 | CB/Emp. Reg. Works 4 days | Yes/No |
| 65. | Days Worked-5 | CB/Emp. Reg. Works 5 days | Yes/No |
| 66. | Days Worked-6 | CB/Emp. Reg. Works 6 days | Yes/No |
| 67. | Days Worked-7 | CB/Emp. Reg. Works 7 days | Yes/No |
| 68. | Days Off-Sat | CB/Emp. Reg. Days Off-Sat | Yes/No |
| 69. | Days Off-Sun | CB/Emp. Reg. Days Off-Sun | Yes/No |
| 70. | Days Off-Mon | CB/Emp. Reg. Days Off-Mon | Yes/No |
| 71. | Days Off-Tue | CB/Emp. Reg. Days Off-Tue | Yes/No |
| 72. | Days Off-Wed | CB/Emp. Reg. Days Off-Wed | Yes/No |
| 73. | Days Off-Thurs | CB/Emp. Reg. Days Off-Thurs | Yes/No |
| 74. | Days Off-Fri | CB/Emp. Reg. Days Off-Fri | Yes/No |
| 75. | Wage | Employee's Current Wage | Number |
| 76. | Wage-Hr | CB/Emp. Wage Per Hour | Yes/No |
| 77. | Wage-Wk | CB/Emp. Wage Per Week | Yes/No |
| 78. | Wage-Day | CB/Emp. Wage Per Day | Yes/No |

TABLE 5-continued

List of Fields For Import/Export Purposes-OSHA-AccExport

| # | Field Name | Description | Data Type |
|---|---|---|---|
| 79. | Wage-Mo | CB/Emp. Wage Per Month | Yes/No |
| 80. | Wage-Yr | CB/Emp. Wage Per Year | Yes/No |
| 81. | DirectMedical | Direct Medical Costs to Company | Currency |
| 82. | EmpCompCosts | Employer Contribution | Currency |
| 83. | EstLongTermCosts | Estimated Long Term Costs to Company | Currency |
| 84. | TotalCompCosts | Total Compensation Costs By Company | Currency |
| 85. | AdminCosts | Administration Costs to Company | Currency |
| 86. | Locale | Co. Plant Location | Text |
| 87. | Company | Company Name | Text |
| 88. | TeamCode | Team Code | Text |
| 89. | TeamName | Team Name | Text |

Note: The file you are importing must include all of the above listed columns in the order and data types. If your file does not originally have all of these fields (which it probably won't), you will need to make a "SPACER" column for each one that is missing and insert them in the correct position. This "SPACER" function will be much easier if you are importing a spreadsheet file, than if you are importing an ASCII text file. Remember, even if your file is an ASCII text file, you can open that text file in Excel or Lotus and use the "Parse" function to separate the information into organized columns. Then import the completed files.

TABLE 6

List of Fields For Import/Export Purposes-SOS Form Data

| # | Field Name | Description | Data Type |
|---|---|---|---|
| 1. | ReportID | Report ID | Text |
| 2. | IncidentID | Incident ID (Auto Counter) | Counter |
| 3. | Last | Last Name | Text |
| 4. | First | First Name | Text |
| 5. | AffectedPerson | Affected Person | Text |
| 6. | WeyerEmp | Is this an Employee? | Yes/No |
| 7. | NonEmp | Is this a Non-Employee | Yes/No |
| 8. | Company | Company Name | Text |
| 9. | Locale | Plant/Location # | Text |
| 10. | Department | Employee Department Code | Text |
| 11. | Dept Name | Employee Department Name | Text |
| 12. | MailStop | Employee Mail Stop | Text |
| 13. | ReportType | Report Type | Text |
| 14. | DOB | Date of Birth | Text |
| 15. | Sex Male | Is the employee Male? | Yes/No |
| 16. | Sex Female | Is the employee Female? | Yes/No |
| 17. | SSN | Social Security Number | Text |
| 18. | Address | Date Employee Hired | Text |
| 19. | City | Check Box/Was Employee Hospitalized | Text |
| 20. | State | Name of Hospital Emp. was taken to | Text |
| 21. | Zip | Date Injury Occurred | Text |
| 22. | LOE | Time Injury Occurred | Number |
| 23. | Hired | Time Employee's been in Dept | Text |
| 24. | DateOfIncident | Emp. Treating Physician | Date/Time |
| 25. | Time of Incident | Part of Employee Body that was Injured | Date/Time |
| 26. | Time in Dept | Check Box/Left side of Emp. Body | Date/Time |
| 27. | Location | Check Box/Right side of Emp. Body | Text |
| 28. | Nature of Injury | CB/Had Emp. Injured Body Part Before | Text |
| 29. | IncidentType | Nature of Employee's Injury | Text |
| 30. | IncidentCode | Cause of Employee's Injury | Text |
| 31. | InjuryCode | Condition that Contributed to Injury | Text |
| 32. | Cause | What Type of Accident Caused Injury | Text |
| 33. | Condition | Description of the Accident | Text |
| 34. | ConditionCode | What Corrective Action Taken | Text |
| 35. | Accident Type | Date the Corrective Action was Taken | Text |
| 36. | Accident Description | Witness of the Accident | Text |
| 37. | CorrectiveActionTaken | Date that Company First Knew of Acc. | Memo |
| 38. | Corrective ActionDescription | Address Where Accident Occurred | Yes/No |
| 39. | DateCorrectiveActionTaken | Nature of Business | Memo |
| 40. | Witness | County where Injury Occurred | Date/Time |
| 41. | DateReceived | Check Box- | Date/Time |
| 42. | DateReplied | Check Box- | Date/Time |
| 43. | ProjectedCompleteDate | Occupation of Employeee | Date/Time |
| 44. | DateCompleted | Length of Time Emp. Worked for Co. | Text |
| 45. | AcknowledgedBy | CB/Was Emp Injured on Premises-Yes | Memo |
| 46. | AcknowledgeNotes | CB/Was Emp Injured on Premises-No | Yes/No |
| 47. | Response-Yes/Completed | CB/Was Accident a Fatality | Yes/No |
| 48. | Response-Yes/TBI | CB/Did Injury Occur on the Job-Yes | Yes/No |

TABLE 6-continued

List of Fields For Import/Export Purposes-SOS Form Data

| # | Field Name | Description | Data Type |
|---|---|---|---|
| 49. | Response-Pending | CB/Did Injury Occur on the Job-No | Yes/No |
| 50. | Response-No | CB/Injury Occur on the Job-Unknown | Yes/No |
| 51. | Response-Other | CB/Were Other Workers Injured | Yes/No |
| 52. | SupervisorInvolved | CB/Acc. a Result of Machine Failure | Text |
| 53. | SupervisorName | CB/Acc. Caused by Someone Else | Yes/No |
| 54. | FurtherActionNeeded | Company's Description of Accident | Memo |
| 55. | FurtherActionSugg | CB/Is 801 OSHA to be Filed | Text |
| 56. | InvestigationAssignedTo | Description of Previous Injury | Text |
| 57. | IncidentLocation | Beginning of Employee's Shift | Text |
| 58. | PreventativeAction | End of Employee's Shift | Text |
| 59. | RecommendedActionDate | Date Employee Left Work | Date/Time |
| 60. | ActualActionApproved | Time Employee Left Work | Memo |
| 61. | CorrectiveActionAssigned | Date Worker Returned From Disability | Text |
| 62. | WorkOrderNo | Number Hrs Employee Works Per Shift | Number |

It will be appreciated that the physical data structure in storage device 14 or RAM 16 may take any suitable form, such as inline or multidimensional arrays, indexed arrays, or indexed tables.

To better explain the system and methods of the present invention, the operating instructions of a preferred embodiment of the invention are incorporated below:

SAFESTAR

Versions 3.0 - 3.NET and 4.0
*Operating Instructions*

Chapter 1

Program Overview:

Developed by STAR SOLUTIONS™ (SSCS), SAFESTAR™ is a Windows™-based software program that allows you to:

- Track corporate safety performances

- Create State & Federally required OSHA forms in 1/30th to 1/60th the time traditionally required (both manually and electronically via Electronic Data Interchange)

- Help meet Federal OSHA time requirements for reporting fatalities or catastrophic injuries.(Avoid expensive fines & violations).

- Administer effective safety awareness incentive programs

- Track and administer training programs

- Track attendance performances

- Support internal safety reporting requirements (including graphs, issuance of safety communication pieces, and multi-type detailed analysis).

- Import and export data from/to other data sources and types.

System Requirements:

In order for SAFESTAR™ to run optimally, it will require a minimum operating system of at least the following specifications:

- 486DX
- 33 megahertz cpu
- Minimum RAM -
    - Using Windows 3.11 - 4 meg RAM (recommend at least 8)
    - Using Windows for Workgroups or Windows NT - 8 meg min. RAM
- Local Bus Recommended
- 1 meg VRAM (recommend at 2 for optimum performance)
- Novell LAN Network or Equivalent

Using This Manual:

To help you make the best use of this manual, we have included the symbols below to set off special information or warnings to which you should pay extra attention. Although relatively easy to understand, you may still want to familiarize yourself with their meanings:

System-Related Issue

Shortcut or Tip

PREPARING YOUR COMPUTER FOR SAFESTAR™

The following items are recommended in order to make absolutely sure your system is "fine-tuned" and ready for SAFESTAR™!

> *SAFESTAR™ was designed with the novice computer user in mind. Its basic structure is based on a "Point-and-Click" format in which you push on-screen "buttons" to get around. With very few exceptions, there is no action that you cannot reverse or back out of!*

VIDEO RESOLUTION: VGA vs. SVGA

SAFESTAR™ has been designed to fit completely in the VGA mode. If you have Windows 3.1 or higher and a SVGA monitor, you can select the Super VGA video driver from the Options menu in the Windows Setup file. It is important to remember that using the SVGA mode is overkill, as it will result in more blank space for most forms. The primary benefit would be found when displaying state and federal forms on-screen.

For optimum viewing and graphic resolution, we recommend that you operate in the VGA mode when using SAFESTAR™.

MEMMAKER:

If you have only 4 megs of RAM and also have DOS 6.0 or higher, you will want to run "MEMMAKER" before installing SAFESTAR™. To do this, exit Windows to the DOS prompt and make the following entries:

cd\DOS [Enter]
    MEMMAKER [Enter]

It's that simple. Just answer the questions on the screen and DOS will do the rest. MEMMAKER is a DOS function that will optimize your memory management and make the maximum memory available for use when running Windows applications.

UTILITIES:

Although not exclusively required for SAFESTAR™, we recommend that prior to installing any Windows program, you run a disk utility program (e.g. Norton, PC Tools, Defrag in DOS, etc.) to defragment your system and correct any file allocation errors that may be present on your hard disk drive.

NEVER DO's:

Never turn off your computer without first closing SAFESTAR™ and exiting Windows. Failure to do so can result in file corruption and memory allocation errors. Although these errors can usually be corrected without any problems, there is a chance that data can be permanently lost.

Installation: (Stand-Alone)

The SAFESTAR™ software consists of four, 1.4m floppy disks (for version 3.1) and six, 1.4m floppy disks (for version 4.0). Before beginning the installation process you must first close all open applications. Once that is accomplished, complete the following steps:

Insert the disk labeled #1 into the floppy drive
Open the File Manager application (found in the Main Menu of the Windows Program Manager).

Open the File menu and click on Run
At the prompt, type: B:\SETUP.EXE (Note: or type the appropriate drive letter where the disk is located). Or - In File Manager, you can opt to Double-Click on the SETUP.EXE file located on disk #1.

The Install Program will prompt you to insert the next disks until complete.

Once installed, you will find the SAFESTAR™ program group in the Program Manager. To start the program use the "switch to function" or double click on the program group.

Once the program group is opened, you will have a choice of two icons: SAFESTAR™ & Repair/Compact.

To start the program, Double-Click on the SAFESTAR™ icon (*See the Utilities section for more information on the Repair / Compact Function)

VERIFY TABLE ATTACHMENTS - ATTACHMENT MANAGER

The data files in SAFESTAR™ are located in tables that are connected by way of a special "attachment manager". This component helps ensure that every time you open the program, all required tables are connected properly. This feature is especially helpful when SAFESTAR™ is being used in a network environment, and the network goes down. By going into the re-attachment section, the user can follow the directions below and re-direct the program to look at a local C (or whatever drive is available) and still be able to use the program even though the main data files are located on the network server that is down. The default setting for these pre-attached tables is C:\SAFESTAR. If at the time of installation, you have installed SAFESTAR™ into any other directory than the one listed above, you will need to open the "VERIFY ATTACHMENTS" section at the MAIN SWITCHBOARD and change the path commands. To do this you need to:

1. Go into the "VERIFY ATTACHMENTS" section (from the Main Switchboard)

2. Change the "Global Path" by clicking on the appropriate icon.

3. Once the "Global Path" dialog box has been displayed, select the "Browse" button.

4. Use the mouse to go to the directory that SAFESTAR™ has been installed in. You should be able to see at least three files displayed: SAFESTAR.MDB, BASICTBL.MDB, & SAFEDATA.MDB.

5. Double-Click on the file named SAFEDATA.MDB.

6. After you have returned to the 'Global Path" change dialog box, select "OK", then "OK" once more.

7. At this point, you will be exited out of the attachment manager and an ATTACHMENT MANAGER dialog box will appear on-screen. This box will ask you if you want to rebuild all attachments and has two options, YES or NO. Select YES.

8. After SAFESTAR™ has checked all tables, it will return a message that there is an ATTACHMENT ERROR. Choose "OK" to modify the file manually.

9. If the ATTACHMENT MANAGER does not immediately re-appear, re-select it from the Utilities section of the MAIN SWITCHBOARD.

10. Repeat steps 1 - 4 and when you come to step 5, choose BASICTBL.MDB instead. Continue with remaining steps.

*Setting up SAFESTAR™*

This manual is designed to follow along with the natural format of the SAFESTAR™ software. This will hopefully make it easier for you to understand the program and find assistance when needed. There are a few tips to help you get started:

1. Enter you company information and complete all set-up forms before attempting to begin entering accident / attendance / training / workers compensation data.

2. Decide whether or not you will be importing your company's employee files into SAFESTAR™. If so, in what format, or will you manually enter the data? Should you decide not import your employee files, you will be limited from producing any one of the reports that is based on / and includes team / department data (e.g. Accident Report by Period, Employee Master Lists by Team / Department). Also, it will take longer to complete many of the forms that already include quick-entry employee / participant lookup fields.

*SAMPLE FILES:*

SAFESTAR™ comes with sample files to allow you to see what the entries, final reports and graphs should look like. After you have familiarized yourself with SAFESTAR's operation, you should select the "DELETE SAMPLE INFORMATION' from the MAIN SWITCHBOARD. You aer now ready to use SAFESTAR™ in a "real-world" environment. Note: Once this function has been performed, do not push the DELETE SAMPLE INFORMATION button again.

*NEW ADDITIONS IN THIS EDITION:*

If you are an existing user of SAFESTAR™ and this is an upgrade, you will find a number of new additions and enhancements. These include:

- Enhanced Accident Report Capabilities
- Advanced Accident Investigation
- OSHA 200-S Year Questionnaire Report
- Safety Observations Category
- Incentive Administration Report Category
- Expanded Accident-Related Graphs (including multiple-year comparisons and design modification capabilities. Over 240 different combinations)
- Multi-Site, Network-Capabilities (Optional)
- Sign-On Security and Password Protection 🐾 Enhanced Screen Design, utilizing "Smart Icons"

We trust that you will enjoy using this program as much as we enjoyed creating it.

Chapter 2

Navigating Around SAFESTAR™ (Overview):

Remember, to navigate your way around SAFESTAR™ you only need to push the on-screen "button", using your mouse 🖱. Upon opening the program you will find yourself at the Main switchboard.

Within the program there are three primary "Switchboards" that you will encounter: "Main", "Main Forms" and "Main Reports". *See the flow-chart below for a complete path breakdown.

SEE FIG. 12

On-Line Help -

An On-Line help system has been provided to assist you in working with SAFESTAR™. To open the Help system, simply press the F1 key. Once opened, you can search for a selected subject by typing the first few letters of the topic. Once a topic is selected, you may view the available options or associated sub-topics. Any help item selected may be copied and/or printed.

Navigation / Control Buttons in SAFESTAR™

Once a form has been selected and opened, you will encounter a row of buttons that assist you in locating and changing file information.

SEE FIG. 13

LOOKUP - The first of these buttons is a "Lookup" window that shows the reference for the current selected data (e.g. employee name, file reference, etc.). By clicking on the small "arrow-down" button on the right side of this box, all available / pertinent records will be displayed. To go to a specific record, type in the first few characters. SAFESTAR™ will highlight the first complete match it finds (at least 3 characters/letters are required). Once a selection is made, the form will go directly to that record.

First / Last / Next / Previous - Immediately to the right of the "Lookup" box are the record navigation buttons. From Left to Right, their functions are as follows:

Button #1 = Go to the first record in the table

Button #2 = Go to the previous record in the table

Button #3 = Go to the next record in the table

Button #4 = Go to the last record in the table

Edit - This button will unlock the current record and allow changes / modifications to be made.

Delete - This button will delete the current single / or multiply selected records. You will be prompted to confirm your deletions at all levels.

Add / New - This button will allow you to add a new record to the table. Once depressed, a blank screen will appear as well as two new buttons at the top of the screen "SAVE" and "RETURN". After you have completed the new record, select SAVE prior to depressing the "RETURN" button. Should you select the "RETURN" button without first pressing "SAVE", the data you have just entered will be lost.

Close - This button will close the current form and return to the appropriate switchboard.

Override: This button is designed to be used in the event that the user accidentally opens a form that requires specific data, and will be prevented from exiting the form until the information is completed.

Exiting Reports and Graphs - In order to exit reports and graphs, you will need to do one of the following:

If a menu is displayed at the top of the screen (e.g. File, Edit, View, Window), then select the "FILE" category and choose the "CLOSE" option.
If no menu is displayed, you may also close by "double-clicking" on the square white box in the upper left hand corner.

Very Important, when exiting a report or graph, NEVER select the "EXIT" option. If you do, you will be exited entirely out of the system and be required to restart the program.

*Main Switchboard:*

SEE FIG. 14

This is the central nervous system of the SAFESTAR™ program. Here you will be presented with several choices:

↑ GO TO THE MAIN FORMS SWITCHBOARD

↑ GO TO THE MAIN REPORTS SWITCHBOARD

-OR-

Perform Any One of Several Utility Functions (ranging Importing / Exporting, Check Table Attachments, Add / Modify Permissions, Delete Sample information, etc.)

In addition, this screen contains an overview of the program (current time/date, # Accidents Entered To-Date, # of Employees enrolled in the program and Est. $'s saved by using SAFESTAR™).

Opening SAFESTAR™ - Each time the MAIN SWITCHBOARD is opened in SAFESTAR™, the program will first run a check of all accident case files and determine whether or not there have been any new reports created within the last 24 hours. If there have been no accidents in this time period, SAFESTAR™ will return the following message:

"There are no new accidents to report. Have a Safe Day!"

If, however, an accident(s) have occurred within the last 24 hours, an ACCIDENT NOTICE box will be displayed at the opening screen. The box lists the number and description of any qualifying accidents and offers the administrator the opportunity to go directly into any one of the new reports, bypassing the switchboard process.

SEE FIG. 15

SECURITY: Passwords and Permissions

Signing-On: Before being allowed entry into SAFESTAR, each user will be prompted to enter a valid SIGN-ON CODE and PASSWORD. After installing SAFESTAR, your SSCS account executive will provide you with a valid sign-on code and password. After the sign-on code and password are validated, the software will determine which files the user is authorized to have access to. To modify the password or assign new users, select the Add / Modify Permissions button at the MAIN SWITCHBOARD.

SEE FIG. 16

Add / Modify Permissions:

Password Protection -

Upon pushing this button, the user will be prompted to enter a valid MASTER PASSWORD before being allowed entry into the permissions group. All incorrect attempts will result in the user being exited from the program. Your SAFESTAR account executive will provide you with the valid password, which you may change after entering the permissions form. IMPORTANT NOTE: When changing your password and pressing enter, you will be prompted to reconfirm your change. You must re-enter the password exactly as it appears above in order to have the change take effect. Once you have changed your password, you will need to re-enter it each time in order to regain access to this section. It is very important that you write down the password and store it in a secure place. Should you lose or forget the new password after it is changed, the only alternative is to contact SSCS for a re-install disk.

SEE FIG. 17

Security / Permissions (Cont.)

Add / Modify New Users: This section allows the program administrator to create / delete authorized users. Pay special attention to the role that the "Asterisk * " plays in this process.

Instructions - Adding / Modifying:

SEE FIG. 18

Step # 1.  Sign-On ID = Any letter / number combination that identifies the user. (required)

Step # 2.  Password = Any letter / number combination (no spaces) that acts as a secondary security level (e.g. dept name, file name, etc.)

Step # 3.  Company = Select a specific company name from the list, or leave the " * " if unlimited access is desired, (note: the " * " is the default value, if you want to restrict the records for this user to a specific company you will need to replace the " * " with a company name).

Step # 4.  Level = Within a given company, select a specific plant / location # from the list, or leave the " * " if unlimited access is desired. (*Same note applies as for the company - see Step #3).

Instructions - Deleting:

Position the curser on the left side of the screen and click on the row which contains the user you wish to delete. You should see the data in that row become dark (highlighted). Press the delete key and select YES when prompted to confirm your changes.

Sign-On Error Log: The system administrator can view / print a sign-on error log which contains all failed attempts to gain entry into SAFESTAR. This section is particularly helpful when contacted by an authorized user who entered and incorrect sign-on. The administrator can review the entries and determined where the error occurred.

*Main Forms Switchboard:*

SEE FIG. 19

This is the platform from which you will open any of the category switchboards that contain entry / input forms. It is divided by these categories:

- ↑ Program / Employee Related
- ↑ Setup Forms
- ↑ Accident Related
- ↑ Attendance Tracking
- ↑ Training Tracking
- ↑ Workers Compensation
- ↑ Safety Observations & Suggestions To go to a desired category, simply press the corresponding button on the screen. You will be directed to another switchboard for that subject. In this screen, you need only select any one of the form buttons on the left, verify its description and push the "OPEN" button to go to that form.

SEE FIG. 20

*Main Reports Switchboard:*

SEE FIG. 21

Just as the "Master Forms Switchboard" is where you will select forms for entering data, this is where you will select the direction for viewing appropriate reports and graphs. Divided by the same categories as in the forms switchboard, the types of reports include:

- ↑ Program / Employee Related
- ↑ Setup Forms
- ↑ Accident Related
- ↑ Attendance Tracking
- ↑ Training Tracking

- ↑ Attendance Information
- ↑ Workers Compensation
- ↑ Safety Observations & Suggestions To go to a desired category, simply press the corresponding button on the screen. You will be directed to another switchboard for that subject. In this screen, you need only select any one of the report buttons on the left, verify its description and push the "PREVIEW" or 'PRINT" buttons in order to view or print that report.

SEE FIG. 22

Chapter 3

Forms

Quick Overview

| Group: | Form Name | Description |
|---|---|---|
| Accident Related | | |
| | Accident Report Form | Entry form for recording accident details |
| | Advanced Accident Investigation | Advanced Accident Investigation entry forms (incl all pertinent accident details as well as training & accident history records, preventative action, and investigative notes) |
| | Corrective – Actions Quick-Entry | Quick-Entry Screen for recorded accidents. Allows the user to enter corrective actions taken and dates implemented. |
| | DMV Report Form | Department of Motor Vehicles - Traffic Accident and Insurance Report Entry area, where accident information can be entered in new or existing reports. |
| | Modify OSHA 200 Log Information | Entry form for all OSHA recordable accidents. Allows the user to input information relative to the OSHA 200 Log (e.g Injury/Illness Types, Days Lost, Fatality, etc.) |
| Program / Employee Related | | |
| | Company Holidays | Enter official Company Holiday Dates (for use in calculating Days Lost) |
| | Company Setup Form | Contains all needed corporate information * Company Name / Address / Fed. ID / Plant Location * Workers Comp. Insurance Carrier Information * State Workers Comp. Department & Address |
| | Department Quick-Entry | Quick-entry change form for modifying employee department information. |
| | Monthly Hours Worked | Enter total staff hours worked on a monthly basis. Allows specification by year and plant location #. |
| | Team Quick-Entry | Quick-entry change form for modifying employee team participation information. (For use in conjunction with a safety awareness incentive program) |
| Attendance Related | | |
| | Absence Codes | Setup form for coding reasons for absences |
| | Attendance Report Form | Entry form for recording absenteeism instances (Includes absence type and corrective actions taken) |

| Group: | Form Name | Description |
|---|---|---|
| Setup Forms | | |
| | Accident Cause Codes | Setup form for Accident Cause descriptions. *Note: This will information will be later used for assistance in internal accident analysis. |
| | Accident Conditions | Setup form for Accident Area Conditions descriptions. *Note: This will information will be later used for assistance in internal accident analysis. |
| | Body Part Codes | Setup form for Affected Body Parts. (e.g. eye, finger, foot, torso, etc.) |
| | Department Codes | Setup form for department codes and descriptions. |
| | Employee Enrollment Form | Comprehensive enrollment form for participants (Note: this data can be imported via the Import Utility in the Main Switchboard) |
| | Incident Type Codes | Setup form for incident types and corresponding codes |
| | Nature of Injury Codes | Setup form for Nature of Injury.(e.g. slips & falls, struck by, etc.) |
| | Occupation Codes | Setup form for employee Occupation descriptions. |
| | Safety Reminder Codes / Descriptions | Entry form for Accident Type & corresponding Safety Reminders. The data in this form is used in the accident report by period - Accident Notice section. Provides a general reminder for each accident type listed. |
| | Team Codes | Setup form for team codes and descriptions. |
| Safety Observations | | |
| | S.O.S. Investigation Form | S.O.S. Investigation form (To be accessed by authorized management personnel only). Allows review and response to submitted S.O.S. report forms. |
| | S.O.S. Report Form | Safety Observation & Suggestion form for use in reporting non-accident related safety issues (unsafe conditions, behaviors or safety suggestions). To report an actual injury or work related illness use the accident form. |
| Training Related | | |
| | Post-Test Scoring Form | Scoring entry form for class participants. Allows the administrator to input the participants' answers to specific test questions. The computer will then evaluate the answer and return a valid score. |
| | Post-Training Test Creation | Entry form for writing post-training class test masters (either 3-option multiple choice or true / false) No limit to the number of questions. |
| | Re-Training Enrollment Form | Enroll persons scheduled for re-training in a specific class & date. Note: Classes may not be added at this level. This entry form is strictly for re-enrollment of a mandatory class. Only eligible participant names will be displayed. |
| | Test Question Summary | Provides a visual test question & correct answer summary for any selected test. |
| | Training Class Enrollment | Entry form for setup up training class information (code, type, description, dates, etc.) and enrolling participants *Note: The enrollment section utilizes a quick-entry format |
| Workers ompensation | | |
| | Accident Cost Entry | Entry Form for recording accident related costs: (incl. Direct Medical, Compensation, Administration, and Estimated Reserves). |
| | Primary Product Definition | Entry form for defining a primary product / service. (incl.: est. MSRP, Avg. Profit Per Unit, Estimated Days to Build / Produce each Unit) |

| Group: | Form Name | Description |
|---|---|---|
| User Permissions: | | |
| | Add / Modify Permissions: | Entry form for adding / modifying or deleting authorized users in the SAFESTAR. Includes password protection and security levels for use in a network / multi-site environment. |

The previous overview has been provided to outline/describe the available forms in SAFESTAR™. The following section covers how to access and utilize specific forms or categories of forms.

Company Setup Form

Description: One of the Primary SAFESTAR setup forms, the COMPANY SETUP FORM contains all of the corporate data required to produce complete State & Federal report forms. Additionally, the form is where key data on multiple locations is stored.

Components:

- Section #1 - Company Information
- Section #2 - Insurance Provider Information
- Section #3 State Worker's Compensation Division Address

SEE FIG. 23

How To Use: In order to complete this form you will need several pieces of information:

- Company Name & Address
- Plant/Location ID. (required)
- Federal ID #
- Industry / SIC Code Information
- Worker's Compensation Insurance Carrier (and affiliated divisions)
- Address of the State Government - Workers Compensation Division

Set-Up Forms -

General Overview

Without exception, those forms included in the "SETUP FORMS" category or within a specific switchboard that are labeled "SETUP" are completed in the same manner. Upon opening each of these forms, you need only to complete the listed fields (e.g. category and/or corresponding code. The majority of the setup forms come to you already pre-loaded with information. You may customize, add or delete fields from these forms (utilizing the command buttons at the top of each form). We recommend that you take time to review these pre-loaded forms and verify that they contain the information you want.

SEE FIG. 24

Employee Enrollment Form

Description: This form is the location for the employee / participant database for all of your participants.

Components: Included in these files are all of the vital information required for the State & Federal OSHA forms (e.g. Name, Soc. Sec. #, Length of Employment, etc.). This form, greater that all of the others, once completed will be the most valuable resource tool in SAFESTAR™.

SEE FIG. 25

How to Use: You have four options available to you for enrolling the participants:

- IMPORT THE INFORMATION FROM ANOTHER FILE (either ASCII or Windows-Compatible environment e.g. Excel, Word, etc.)
- ENTERING THE INFORMATION MANUALLY
- CONTRACTING SSCS to enter the data for you on a per-name transaction basis
- ELECT NOT TO PRE-ENROLL the Participants and Simply fill out the information on the Accident Form Manually

IMPORTING DATA:

To import data, go to the Main Switchboard and select the "IMPORT DATA" button. Before beginning the import process, you are provided the opportunity to print any of the available table import templates. These templates provide important information on the name, position, size and data types of each of the table fields / categories *See example below*. Although it is the easiest and most time efficient way to complete your employee files, this function can potentially provide some of the greatest errors to be encountered in the program. It is very important that the data that is being "imported" into the program be found in the exact column format as the "form" is designed in SAFESTAR™.

SEE FIG. 26

Failure to do so will result in merge errors that cannot be reversed. Instructions are also included on each printed template.

Once into the main IMPORT section, you will be prompted to select the data-type of your file( e.g. ASCII, EXCEL, LOTUS), the location of the information to imported and the destination table in SAFESTAR™.

Importing into Table Name: MASTER NAMES

SEE FIG. 27

Special Note: One of the "Fringe" benefits of this particular form is that the information can be exported and used for other functions outside of the SAFESTAR™ program.

SEE FIG. 28

EXPORTING DATA

To export data, go to the Main Switchboard and select the "EXPORT DATA" button. Within this dialog box you will be prompted for three (3) things: one, Verify that you really do mean to export a specific file (click on the button in the top right of the box); two, Specify the destination file name (full path, e.g. C:\INFO\TEST.TXT) for the exported data (any 8-digit character string, followed by ".TXT*"; three, select the table that you will be exporting (from the pull-down menu).

SEE FIG. 29

*EXPORT DATA TYPE NOTE: Unlike the import process where you can import any one of three different types of data files (ASCII, EXCEL, LOTUS), the export process will output the data in an ASCII "comma-delimited", flat file. That is the reason for the .TXT file extension that you will give to the exported file name.

When the process has been completed, the dialog box will close and you will be returned to the MAIN SWITCHBOARD.

TIP: As the exact exported file size will be unknown, we recommend that you create a temporary directory on your hard drive prior to copying it to a floppy disk. Should the file be larger in size the 1.44 meg, you will have the opportunity to "zip" or compress the file without receiving any errors and having to start over.

*ACCIDENT REPORT*

Description: This form is the cornerstone for the SAFESTAR™ program. It is the source for all accident related reports and graphs. The more information you include, the more complete your reports will be.

Components: There are three primary and 2 secondary sections in the ACCIDENT REPORT FORM:

- SECTION # 1 - Vital Statistics
- SECTION # 2 - Basic Accident Details
- SECTION # 3 - State First Report of Injury and OSHA 200 Log Report Information
- SECTION # 4 - Secondary Causes / Conditions / Witnesses
- SECTION # 5 - State Exceptions

Special Note: There are two components to this report that are ABSOLUTELY required: Last Name, and Date of Injury. Although important, the remaining fields may be completed at a later time. Upon closing the form, the program will check to determine whether data is contained in the Last Name field and the Date of Injury. If these fields are not complete, you must finish them prior to being allowed to exit the program.

How To Use: The Basic Procedure covers the following areas -

SECTION # 1 - Vital Statistics

SEE FIG. 30

1. Select the Accident Report Form from the Accident Related Switchboard
2. Tab once, or Click on, the Social Security # box (Highlighted in Yellow) or (if you don't know the participant's Soc. Sec. #T) tab once more to go to the Name Lookup Box.
3. Push the button with the arrow on the right side of the box. You will see the entire list of saved social security numbers, employee ID's or names & Soc. Sec. #'s.
4. Enter the first 2 -or- 3 digits or letters of the last name. This will bring up the Soc. Sec. # or name that most closely matches the first three numbers you entered.
5. If the number or name you are looking for appears, double click on it in this field.

The program will search the employee / participant database and return answers to most of the vital information fields. Once the vital information section has been completed, select Page Down to go to the Report Specifics section.

Note: At least the last name and locale (plant / or location) are required on this first screen.

SECTION #2 - Basic Accident Details

How To Use: Complete the requested information, using the "Pull-Up" boxes for any of the listed categories. Note: It is important to note if you intend to produce the Accident Report By Period report, you will need to select / include an item from the Accident Reminder category. In addition to the fields in this section, the following boxes have special significance:

SEE FIG. 31

Is an Investigation Required?: If the accident meets your company's requirements for an accident investigation, click on this box (an "X" will appear).

SEE FIG. 32

Is a First Report of Injury Required?: One of the last questions you will encounter in the Report Specifics section, answering "Yes" will make visible the FROI / OSHA control button on the screen. If the accident is recordable, continue to the next section:

SEE FIG. 33

Sub-Section # 1 - Secondary Causes / Conditions / Witnesses

In addition to the primary causes / conditions and witnesses entered into this portion of the reporting process, the user also has the ability to add secondary causes / conditions and witnesses in a separate form. To access this screen, simply press the button located beneath the CAUSE entry box. Once in this screen, you may select as many additonal items from the pull down menus. The next time you open this section, your previously selected choices will be displayed in the summary boxes below.

SEE FIG. 34

SECTION # 3 - State First Report of Injury and OSHA 200 Log Report Information

TIP - EMPLOYEE DESCRIPTION: If there is little or no variation between the COMPANY ACCIDENT DESCRIPTION and this field, you can simplify the process by copying and pasting the company accident description from the previous section (select copy from the Edit menu on the toolbar).

SEE FIG. 35

Sub-Section # 2: State Exceptions-

If the state to which the employee is registered (via Plant / Location #) requires additional information above thst which has already been entered, an exceptions form will open and the user will be prompted to complete the appropriate fields.

SEE FIG. 36

OSHA 200 Log Information: Once this button is selected, you will be prompted to acknowledge whether or not this accident meets the criteria required for inclusion on the Federal OSHA 200 Log. If you select yes, the OSHA 200 Log section will be displayed.

SEE FIG. 37

The first section of the OSHA 200 Log includes a synopsis of the accident as an Accident Recap in easy to read WHAT, WHEN, HOW BAD, & HOW LONG. This is provided to assist you in entering the one-line accident description for the OSHA200 form. Remember, you have very little room in which to enter a description.

SEE FIG. 38

This section also contains a field for entering a unique case number as well as navigation buttons that will take you to appropriate next category (depending if this is an Injury or Illness).

Injury Section - If you have completed the DATE WORKER LEFT and DATE WORKER RETURNED as well as the SCHEDULED DAYS OFF fields in the OSHA Accident Section in the ACCIDENT FORM, SAFESTAR will calculate and complete the # of days lost categories in the injury section. The only manually entered fields in this section are the date of fatality and # of Restricted Work Days.

SEE FIG. 39

Illness Section - All of the required components for this section have been included in easy to enter on-screen fields. To complete, simply check the appropriate boxes / fields.

SEE FIG. 40

*Advanced Accident Investigation*

Description: Accident cases are added to this section if the "INVESTIGATION REQUIRED?" box in the ACCIDENT SPECIFICS section of the Accident Form has been selected. Designed for the accident investigator who has limited knowledge of a specific accident report, this form provides a comprehensive analysis of all components (incl. status reports, accident specifics, training and previous accident history, and corporate performance analysis).

SEE FIG. 41

Components: Within the Advanced Accident Investigation form there are three sections:

- Vital Information
- Accident Details
- Training / Special Information

How to Use: Upon opening the form, the investigator will see the vital information of the person having the accident as well as a visual, colored "Status" bar indicating at what stage various components of the accident are in.

The next section details the accident specifics (what, where, when, how long, how bad, etc.). It also contains a PROBABLE ROOT CAUSE field in which the investigator can add / modify the probable root cause of the accident. Additionally, the investigator will see how many other accidents in SAFESTAR match each of the criteria (eg. nature / body part / condition, etc.)

SEE FIG. 42

Within the Training / Special Information Section, the investigator is provided with four (4) primary components:

- A complete training history of the employee (incl. Dates of classes and scheduled re-training)
- A complete accident history (incl. All other accidents / dates / etc.).
- Investigator Notes Section ▶ An Accident Performance Analysis. This section calculates the avg. number of accidents per employee, the number of accidents that this employee has had and finally what "Percentage" of performance (e.g. 50% or 300% of the company average).

TIP: Upon opening the Training / Special Information section, the investigator may close the "Investigator Note" box by "double-clicking" on the white box in the upper left-hand corner. To re-open this note box, it will be necessary to go back to the Accident Specifics section and then re-open the Training / Special Information section.

SEE FIG. 43

*Corrective Actions (Quick Entry)*

Description: This form can be used a quick-reference for the program administrator to be able to review those accidents for which no corrective actions have been taken to date. It also serves as a "Quick Entry" screen for entering subsequent corrective actions once they have been completed.

SEE FIG. 44

How to Use - records can be accessed either via use of the lookup box or by simply scrolling down the list via use of the vertical scroll bar on the right side of the screen.

TIP: *Also See Corrective Actions Not Taken Report in the Reports Section.*

*DMV Report Form*

Description: This Department of Motor Vehicles (DMV) form allows for the reporting of vehicular accidents and all related components. Very comprehensive, the DMV form includes a majority requested accident items (incl. driver, passengers, all vehicles, accident descriptions, weather conditions, insurance information, hospitalization data, etc.)

SEE FIG. 45

How To Use: Upon opening the form, select the involved employee from the pull-down box on the left side of the screen. Once selected, all pertinent employee data will be downloaded into the "DRIVER 1" section. You may navigate easily between the screens by depressing the appropriate buttons.

TIP: For ease in form completion, you need only open / complete those sections that are pertinent.

*Department / Team Quick Entry Forms*

Description: Much like the CORRECTIVE ACTIONS QUICK ENTRY form, these two forms allow the user to quickly modify the department or team information for all enrolled employees / participants.

SEE FIG. 46

How To Use: If a "blanket" change is being made to an entire department number / code, select the find & replace feature under the EDIT menu at the top of the screen. Enter the number to find and then the number that will be the replacement and select REPLACE ALL in the options section. SAFESTAR™ will search and replace all department numbers and their subsequent department names simultaneously.

SEE FIG. 47

TIP: Prior to changing all affected records, you will be prompted to verify changes. Once changes have been made, they cannot be undone, but the process can be repeated to replace the previous number / code that was changed.

Monthly Hours Worked

Description: Found in the Company / Employee Related section, the MONTHLY HOURS WORKED entry form plays an important role in producing a dynamic "Master Accident Performance" report in the reports section. This report will calculate the incident / frequency / severity rates for a specified company or division.

SEE FIG. 48

Components / How to Use: Categorized first by year, then by locale, the MONTHLY HOURS WORKED form is divided into company / locale information and then the months are categorized into quarters. Each quarter may be accessed by selecting the appropriate buttons at the bottom of the screen.

SEE FIG. 49

TIP: In order to produce a "Master Accident Performance" report that will calculate a "best-case" analysis through the end of the year, all months must be completed (even though the exact information may not be available). Providing estimates based on past year / month performance is a good way to project these performance numbers.

Safety Observations - Report Form

Description: The SAFETY OBSERVATIONS report form is designed for reporting non-recordable accidents (e.g. unsafe acts, near misses), unsafe conditions and safety suggestions.

SEE FIG. 50

Components: An abbreviated and modified version of the ACCIDENT REPORT FORM, there are only two primary components:

- Vital Information
- Report Specifics

SEE FIG. 51

How To Use: Much like the ACCIDENT REPORT FORM, at the opening screen, the user selects an employee name from the list (or may enter a non-employee in the appropriate boxes) and completes all relevant data. In the Report Specifics section, all basic information is entered and once completed, the form is closed.

Safety Observations - Investigation Form

Description: The second phase of the SAFETY OBSERVATIONS section, the Investigation Form picks up where the initial report left off.

SEE FIG. 52

Components / How To Use: In this form, the investigator will first be presented with a vital statistics overview and component status review. In the subsequent screens, the incident details and opportunity to determine a probable cause are provided. The last section involves reporting of all actions taken and acknowledgments / work orders issued (where applicable).

TIP: *Also See: Safety Observations Report & Investigative Report in the reports section.

Training Class Enrollment Form

Within the TRAINING CLASS ENROLLMENT FORM, there are three sections:

- Class Code / Description (incl. re-training interval)
- Date of Class (incl. Date / Time, Instructor, Test Code, Location, & Date Navigation Buttons)
- Training Class Participants (incl. Quick Lookup)

SEE FIG. 53

How to Use:

New Classes - Open the form and select NEW to go to a new class creation screen. Fill in all pertinent boxes and tab to the Date of Class Section.

Existing Class - Select an existing class code from the lookup box at the top of the form. Once you have been moved to the selected record, modify the data as needed (e.g. add new dates, enroll new students

Enrolling Attendees - Select an employee name from the NAME LOOKUP box in the CLASS PARTICIPANTS section. Once selected, SAFESTAR will lookup the employee's vital information and automatically complete the remaining fields.

TIP: In order to navigate between class dates, select the Next Date or Previous Date buttons to move back and forth in the class dates section. Select CREATE NEW DATE to add a new class date.

Re-Training Class Enrollment Form

Description: Once an employee / participant has been enrolled in a class for which a RE-TRAINING interval has been listed, their name will appear on the re-training list, for the correct class / time period allotted in the future. Although RE-TRAINING CLASS ENROLLMENT FORM appears very similar to the TRAINING CLASS ENROLLMENT FORM, the difference can be found when the NAME LOOKUP box is selected for a particular class, on a particular date. If there are any persons who are scheduled for retraining on/before the date of the class, their names only will appear in the lookup box when it is opened. If this box is blank when opened, the indication is that no one is scheduled for training on/before this class' date.

SEE FIG. 54

Post-Training Test Creation Form

Description: The POST-TRAINING TEST CREATION FORM allows the user to create a customized post-training test within SAFESTAR.

Components: The components of this form include:

- Test Name
- Description
- Question
- Possible Answers (incl. Multiple-choice or true/false)
- Correct Answer Identification

SEE FIG. 55

How To: In order to successfully create a post-training test, the user may open this form and select "NEW" or work on an existing test. After the test question has been created and possible answers entered, the user need only to click on the button immediately to the left of the possible answers, where the answer is correct. You may have only one correct answer per question. For True/False, leave the third box blank and enter TRUE as the first answer and FALSE as the second answer.

Post-Training Test Scoring Form

Description / How To: Once an employee or participant has completed and submitted their individual test for scoring, this form allows the program administrator to input the tested person's answers in the "ANSWER" box. Based on the inputted answers, the form will automatically evaluate the performance and return a score at the bottom of the screen. This form may be referenced at any time in order to review an employee / participant's performance.

SEE FIG. 56

Test Question Summary

Description: More of a report that a form, this section will provide a summary of all created test questions for a given test. It is an excellent place to review the work to-date on a particular test in a summary view.

SEE FIG. 57

Accident Cost Entry Form

Description: A manual entry screen that allows the user to input costs associated with each applicable accident. This information is used in producing a MASTER COST ANALYSIS management report that calculates the amount of product / service that will be required in order to pay for the accident (incl. Short - & long-term costs).

SEE FIG. 58

How To Use: Within this form, you will input the identified cost items (direct medical, employee compensation, administration costs and estimated reserves). The initial costs sub-total will be calculated automatically. Because this is an automated function, it requires that all preceding boxes be completed. Even if a category's value is $0.00, please enter a $0.00 amount in that box. These figures may be updated or modified at the user's discretion.

TIP: This is a pre-requisite form for the Master Cost Analysis report.

Primary Product Definition

Description: This form is basically used as a "SETUP" form in which you enter your primary product /or service and input the indicated financial categories.

SEE FIG. 59

TIP: It is a pre-requisite form for the Master Cost Analysis report.

ATTENDANCE FORM

Description: Completed in much the same way as the ACCIDENT REPORT form, this one screen ATTENDANCE FORM is used to track instances of absenteeism, tardiness, medical or family emergencies.

How To Use: After opening the form, simply select the correct Soc. Sec. # or name and fill in the appropriate boxes. Push Close when through.

SEE FIG. 60

*OSHA200 Log Entry Form*

Description: This form is used for adding / modifying / deleting those accidents that were indicated in the ACCIDENT REPORT FORM as being OSHA 200 recordable.

How To Use:

Entering / Modifying Information - Section # 1:

Upon opening, the program will display the OSHA200 Information form. The only required box for you to complete in this first section is the unique "CASE NUMBER" field. The other participant vital information will have already been automatically entered from the Accident Report Form.

SEE FIG. 61

Accident Recap -

When selected, a synopsis of the accident will appear in the Accident Recap screen in easy to read WHAT, WHEN, HOW BAD, & HOW LONG, in order to assist you in entering the one-line accident description for the OSHA200 form.

SEE FIG. 62

Accident Statistics Injury / Illness - Section #2:

The section you will complete is dependent on whether the accident involved an Injury or and Illness. Select the correct category from the main OSHA 200 information screen. As with all of the forms, check the correct boxes until all necessary portions are complete. When you are through, you may close the form.

SEE FIG. 63

Chapter 4

*REPORTS*

Overview

| Group | Report Name | Description |
|---|---|---|
| Accident Related | | |
| | Accident - Supervisors Report | Produce an internal \Supervisor's Report of Occupational Injuries and Illnesses\. Can also be used as an internal accident report. |
| | Accident Analysis Defined | Accident analysis based on user-defined parameters (e.g. dates / types / causes, etc.). |
| | Accident Report - Corrective Actions Not Taken | List of all accidents for which corrective actions have not been implemented. |
| | Accident Report By Period | Detailed listing of all reported accidents that occur between two user-specified dates. (Incl. Accident synopsis, persons in department, accident notices) |
| | Accident Synopsis by Period | Provides a synopsis of all accidents that occur between two user-specified dates. |
| | DMV Report | Department of Motor Vehicles - Traffic Accident and Insurance Report. This report gives accident details, vehicle, passenger, and insurance information. |
| | Master Accident Performance | Comprehensive performance report including: Mo Hrs Worked, Incidents, Frequency & Severity Rates. |
| | Master Accident Report | Listing of all recorded accidents (Chronologically by Month & Alphabetical Participant Listing). |
| | OSHA - Yr. End Questionnaire | Produce the OSHA Year-End Questionnaire section entitled \Cases with Days Away from Work\ for each applicable accident. User Parameter Defined |
| | OSHA 200 Log | Annual OSHA 200 Accident Log. (Can be parameter defined by Company / Locale / Department) |
| | State First Report of Injury | Comprehensive, individual First Report of Injury (By State). User-Defined. |

| Group | Report Name | Description |
|---|---|---|
| Accident Related Graphs | | |
| | Accidents - Avg. Costs | Calculates the AVERAGE COSTS by Injury. (BAR GRAPH) |
| | Accidents - By Body Part | Overview of all accidents, sorted by BODY PART involved(BAR GRAPH) |
| | Accidents - By Day of the Week | Presents an accident analysis by \Day of the Week\. (Pie-Chart) |
| | Accidents - By Department | This graph shows the accident totals by DEPARTMENT. (BAR GRAPH) |
| | Accidents - By Department (Percentage) | Calculates the percentage of accidents incurred by department. (PIE CHART) |
| | Accidents - By Length of Employment | Accident breakdown by Length of Employment. (PIE-CHART) |
| | Accidents - By Nature of Injury | Breaks down accidents by NATURE of INJURY. (BAR GRAPH) |
| | Accidents - By Specific Safety Reminder Types | This detailed graph shows accidents by ACCIDENT REMINDER, breaking them down into the month in which they occurred. (3-D AREA GRAPH) |
| | Accidents - By Time of Day | Presents an accident analysis by \Time of the Day\. (3D-Column) |
| | Accidents - Costs - Hi/Lo | Presents all the accident claims (high - to- low) whose COSTS were over $100. (LINE GRAPH) |
| | Accidents - Monthly Totals | Breaks down total accident counts by MONTH. (LINE GRAPH) |
| Attendance Related | | |
| | Attendance Report By Period | Detailed listing of all reported absenteeism instances that occur between two user-specified dates, (incl. List of all persons in department). |

| Group | Report Name | Description |
|---|---|---|
| Program / Employee Related | | |
| | Basic Employee Report | Alphabetical list of all enrolled employees. Includes basic information: (Name, ID, Hire Date, Department, LOE). |
| | Master Employee List (By Department) | Employee list sorted alphabetically by Department or Shift and last name. Includes the same data as the Master List. |
| | Master Employee List - By Team | Employee list sorted alphabetically by Team. |
| Program / Employee Related(cont.) | | |
| | Master Employee Report | Complete Alphabetical list of employees. Includes all personal data (address, phone, etc.). |

| Group | Report Name | Description |
|---|---|---|
| Safety Observations | | |
| | Safety Observations - Analysis | Safety Observations report analysis based on user-defined parameters (e.g. dates / types / causes, etc.). |
| | Safety Observations - Corrective Not Taken | Details all Safety Observation Incidents for which corrective actions have not been taken. |
| | Safety Observations - Investigation | Safety Observation Report - Investigation Report. (Incl. Recommended actions, final dispensation, work order no.) |
| | Safety Observations - Master Report | Master SAFETY OBSERVATIONS Incident Report |
| | Safety Observations - Nature of Incident | Master SAFETY OBSERVATIONS report by nature of incident (user-defined parameters) |
| | Safety Observations - Preventative Actions | Analysis of preventative actions taken for all SAFETY OBSERVATIONS reports. |
| | Safety Observations - Report | Safety Observation Report - Confirmation / Response form. |
| | Safety Observations - Status Report | Produces a Visual-Status report of all Safety Observations reports / investigations on file. Note: It is an excellent report for quick review. |
| | Safety Observations - Synopsis | SAFETY OBSERVATIONS report synopsis. (Sorted by user-defined dates). |

| Group | Report Name | Description |
|---|---|---|
| Training Related | | |
| | Master Employee Training Report | Alphabetical Listing of All Participants who have participated in Co. sponsored training classes. (Incl. Name, Classes Attended, & Class Totals). |
| | Master Safety Reminder Report | Alphabetical Listing of all injury Reminders currently on file. |
| | Master Training Class Report | Alphabetical & Chronological listing of all Employee Training Classes. (Incl. Class Code, Name, Description, & Participants). |
| | Re-Training Master Report | Master Re-Training Report: Shows scheduled re-training records for all enrolled employees |
| | Training Class Notices | Provides notices of Scheduled Training Classes. Parameter Defined by Class Specific. |
| | Training Class Roster | Creates a Training Class Roster for use in tracking actual participants. Provides a space for signatures. |
| | Training Records - By Employee | Training report by employee specific. User Defined. |
| | Training Test Issuance | Post-Training Class Tests by Class (user-defined). Issued a hard-copy test for each individual that attended the selected class (alphabetical). |
| Workers Comp. | | |
| | Master Cost Analysis | Comprehensive cost analysis of each accident. Incl. Amt of Product required to pay for an accident claim. User- Def |

| Group | Report Name | Description |
|---|---|---|
| Incentive Program Administration | | |
| | Length of Service - By Year | Master Report - Length of Service. Lists all persons whose length of service falls between the user-defined year range. |
| | Length of Service - By Month | Length of Service - Anniversary Dates. This master report lists all anniversary dates categorized by month. |
| | Accident Free Performance | Master Report of those persons who have performed "accident free" for a period of tim greater than indicated by the user. |
| | Birthday Analysis | Birthdate Analysis. This report categorizes birthdates by month for all employees. |

The previous overview has been provided to outline/describe the available reports in SAFESTAR™. With exception of the following reports, each report may be accessed in the Preview or Print mode minimal specification or without any additional entries.

Accident Related:

ACCIDENT REPORT - BY PERIOD (Report)

Description: A completely User-Defined report, the ACCIDENT REPORT BY PERIOD is very comprehensive. The report will generate a detailed listing of any accidents that have occurred during that period (by department or team) including an

- Accident description
- Accident type
- Corrective action taken.

Immediately following the accident summary, a listing of all persons from that employee's department is provided. The final section produces an accident notice for each person in that respective department. This notice outlines:

- A general description (anonymous),
- An accident type
- Corresponding safety reminder for the specific type of injury.

SEE FIG. 64

How To Use: When you select this report you will be prompted to enter the Period Start and Period End Dates (Include any mo/day/yr) as well as be able to specify any one of five related categories, and specify by company / locale / department. Based on the information given in these boxes, the program will search the accident files and create a report that lists any accidents (by dept.) and all persons in the department in which the accident occurred.

TIP: In order to produce the ACCIDENT NOTICES, a safety awareness reminder must first be entered in the report specifics section of the ACCIDENT REPORT FORM. This report is also one of the PRIMARY tools for administering a successful and comprehensive SAFETY AWARENESS INCENTIVE Program. *Also See the INCENTIVE RELATED Section on the Reports Switchboard.*

Accident Analysis Defined

Description: This is one of the most comprehensive accident analysis reports in the system. Designed to replace most "ad-hoc" report requests, the ACCIDENT ANALYSIS DEFINED report allows the user to define / request an accident analysis report based on one or all (in any combination) from the following criteria:

- Nature of Injury
- Accident Type
- Accident Cause
- Accident Condition
- Company
- Locale
- Department
- Reporting Start & End Dates

SEE FIG. 65

State First Report of Injury

Description: A complete print-out of the individual state's "FIRST REPORT OF INJURY". Submitted to the state workers compensation division, this form eliminates the need to manually produce a carbon-form report ever again.

How To Use: You will be prompted to select a case from the pull down menu. Once selected, the name and date for the person you just entered will be displayed in the confirmation boxes. From this point, you may select either the Preview or Print options.

SEE FIG. 66

Note: This report may contain graphic files that will cause it to take a considerable amount of time to print (2 - 5 minutes). Where required, an "Employee Receipt" will be automatically be included with the master report.

Depending on your internal policies for # of copies, you will need to make multiple copies of the full State First Report of Injury report and distribute to the appropriate departments.

OSHA 200 Log REPORT:

Description: This report produces the annual OSHA 200 Log (specified by Company / Locale / Department).

How To Use: Enter the year to process at the prompt and

SEE FIG. 67

VERY IMPORTANT - In order to be able to even view this report, the HPIIP print driver (*See the Configure Printers Section) must be installed. After the printer driver screens have been displayed, you will be prompted to enter the year as well as company / locale / department (where applicable).

Once the printer driver is loaded, the report will be displayed in the landscape view, legal size (8 1/2 in X 14 in). Preview the information on-screen. If any changes need to be made, you can make them in the "ENTER OSHA 200" form. REMEMBER to put a legal size piece of paper in the printer prior to printing.

OSHA - Yr End Questionnaire

Description: Also known as the 200-S form, the OSHA -YR END QUESTIONNAIRE report reproduces the federally mandated form for reporting cases that involved days away from work. When researched and completed manually, this function is made doubly hard by the additional fact that the scope of the request varies from year to year and requests information only on accidents that fall within a random month and days of the month period.

How To Use: At the prompt, enter the Year to Process, Starting & Ending Months, and Starting and Ending Days.

SEE FIG. 68

Accident Related Graphs

Description: The ACCIDENT RELATED GRAPHS report section offers dynamic, graphical views (both by single year and multiple-year) of your company's total accident related performances. With over 240 possible, different combinations, there is little information that is not covered in this section.

How To Use:

Single Year -

1. Enter the year to process in the YEAR box at the top of the form
 2. Select a graph to view / print Select any one of the three available options: Preview , Print , Design

SEE FIG. 69

Multiple-Year -

1. Depress the MULTIPLE YEAR COMPARISON button at the top of the form.
 2. Enter the starting year to process in the first YEAR box on the Left
 3. Enter the ending year to process in the second YEAR box on the Right
 4. Select a graph to view / print
 5. Select any one of the three available options: Preview , Print , Design

SEE FIG. 70

Design Option: In order to successfully modify the appearance of your graph, you need to be familiar with designing graphs found in most Microsoft programs (e.g. Word or Excel). When you select this option, the graph file that is displayed is not visible, but a blue instruction box appears, follow these steps and you will be able to complete the re-design process:

1. "Double-Click" in the main area of the graph (White Screen)
 2. Your view will be converted to the graph design screen (Graph is made visible).
 3. You can click on any of the menu options (e.g. gallery, chart, or format) and change the appearance, style, text or graphic types.
 4. When you are through making any changes, select "EXIT" from the "FILE" menu. (Note: this is the only time you will ever select the exit option from a FILE menu in SAFESTAR. In this instance, it is being used only for exiting from the Microsoft Graph manager.
 5. You will be returned to the main area of the graph (White Screen).

6. If you have made any changes, upon closing the graphs, you will be prompted to save those changes. Select Yes and Close the form.

*Attendance Related Reports -*

*Attendance Report Period Analysis -*

Detailed listing of all reported absenteeism instances that occur between a user-defined time period. Includes a synopsis of the absenteeism incident and lists all of the persons who work in the department with that individual.

Support Forms Required to Be Completed:
- ❑ Attendance Report Form
- ❑ Primary Product Defined (Workers Compensation Related)

*Workers Compensation Related Reports:*

Master Cost Analysis

Description: Also parameter defined, (e.g. one or all of the following: Nature of Injury, Cause, Condition, Accident Type, Company, Locale or Department), the user can produce this comprehensive cost analysis of each accident. This is very helpful when evaluating the "bottom-line" impact of any accident and then to translate it into "how much product or service" will we need to manufacture or support in order to pay for not only the short-term "hard-costs", but also what are the long-term ramifications if *We can't return this person to his/her position right away.*

SEE FIG. 71

Support Forms Required to Be Completed:
- ❑ Accident Report Form (Accident Related)
- ❑ Primary Product Defined (Workers Compensation Related)

Chapter 5

*UTILITIES*

*Printer Configuration -*

In order to be able to print the OSHA200 Annual Report, you must install, or have loaded the HPIIP laser printer driver. This driver is accessed through the Main group of the Program Manager. In MAIN, you will find the computer icon labeled "CONTROL PANEL". Double-clicking on this icon will display the CONTROL PANEL options, one of which if the PRINTERS. Double-Click on this icon and select "Add", following the instructions on the screen. You will need to have disk # 6 of the Windows program disks. All other reports are set to print on your default printer set through windows.

REPAIR & COMPACT

Besides running regular disk utilities on the entire system, we recommend that you run the REPAIR/COMPACT utility (found in the SAFESTAR™ Program Group).

BACKUP

You should back up the information in the SAFESTAR™ directory weekly (daily is preferred). There are several options available. As mentioned earlier in this manual, any of the disk utility programs, the DOS function "BACKUP" or Windows "BACKUP" (from the file manager) can be used successfully.

TROUBLESHOOTING

Message: "Not Enough System Resources to Update View"

Solution: Exit SAFESTAR™ and make sure all other Windows programs are closed, then try again. If the problem continues, restart SAFESTAR™ and go directly to the report or form and attempt to reopen.

Cause: This error message will occur most often on systems with only 4 meg of RAM. You may want to consider upgrading the system memory to 6 or 8 meg. Also, if you have had Windows open for an extended period of time and have been running any of the standard memory-intensive programs (Word, Excel, Word Perfect, Access, etc.) you may be encountering a problem with conventional resources. You can check this by exiting to PROGRAM MANAGER and viewing the ABOUT file under the HELP category. This ABOUT screen will indicate the percentage of system resources available. Optimum performance with SAFESTAR™ can be achieved when there is at least 60% available. If there is any less than this amount, exit PROGRAM MANAGER and restart Windows.

Message: : "You must first enter a LOCALE # for this employee in the Accident Report form. Please enter the information before attempting to re-open this file"

Cause: This message occurs as a result of a missing locale # in the Accident Report form.

Solution: To correct this error message, re-open the accident form and enter a valid "LOCALE #" in the appropriate box.

Message: : "You must have the DEVELOPERS version of Microsoft Graph!"

Cause: This message occurs when the user attempts to modify the design of a graph in the Accident Related Graphs section.

Solution: In order to complete this function, Microsoft Office Professional™ must be loaded and active on the user's system. This design category utilizes the graph engine included with this suite of products. The ability to modify the pre-built graphs is not a requirement. It has been provided as a service to those persons who have the necessary software to accommodate this request.

Given the above description of the present invention, it can be seen that it includes a data flow as shown in FIG. 11. Specifically, a system database creator/modifier 76 operates on system database 52a to create or modify system database 52a. Creator/modifier 76 includes an input form selector 78 that accesses database 52a and, through VDT 20 and keyboard 22/display cursor control system 24, allows the user to select an input form for display on VDT 20. Once such an input form is selected by selector 78, an input form formatter 80, operating in digital processor 12, formats the selected form for display on VDT 20. The selected is then displayed on VDT 20, and a system record editor 82, through keyboard 22 and display cursor control systems 24, allows a user to select specific records for viewing and editing through the selected form, and input new records using the selected form.

An incident database creator/modifier is shown at 84, again operating through digital processor 12. A system record extractor 86 extracts predefined records from system database 52a, after which a system information extractor 88, operating through VDT 20, keyboard 22 and/or display cursor control system 24, extracts predefined information from the selected records, and allows the user to specify specific information for extraction. An incident record selector 90 operates on incident database 52b, either before, while or after the system records and information are extracted at 86 and 88, to select a specific incident record for viewing or modification or creation. This viewing, modification or creation is performed by an incident record editor 92, operating through digital processor 12, RAM 16, VDT 20, keyboard 22 and/or display cursor control system 24. Once the selected incident records are edited, the information is rewritten to incident database 52b.

A report generator is shown at 94, again operating through digital processor 12. Generator 94 includes a report format selector 96 that accesses system database 52a, and through VDT 20, keyboard 22 and/or display cursor control system 24, allows a user to select a defined report format. Once the report format is selected, a report formatter 98 accesses and extracts information specified in the selected format from database 52, including system database 52a and incident database 52b, and manipulates the information to create a completed report. The completed report is then produced through a computer output medium at 100, such as a printer.

From the forgoing identification of the components of the present invention, the following methods and systems are included within the scope of the invention.

A computer-implemented process of reporting safety information stored in computer memory is controlled by one or more user workstations 10. The process includes the step of creating a system database 52a stored in computer memory 14/16, database 52a including a plurality of defined lists of entries for selected variables and a plurality of defined formats for selected reports. The defined lists include information such as a defined list of employees and a defined list of types of incidents. The defined formats include reports such as OSHA report 200 and DMV (Department of Motor Vehicles) accident reports.

The process also includes the step of creating an incident database 52b stored in computer memory 14/16 by selecting an record from one or more of the defined lists in system database 52a and inserting the selected entry or entries into a data record. This step can include or be concurrent with the steps of accessing previously created incident records, selecting ones of such records to match information inserted into the current incident record, and displaying on the selected form information comparing the current record to the selected ones of the previously created records.

The process further includes the step of creating an incident report by selecting one of the defined formats from system database 52a extracting and manipulating information from incident database 52b as defined in the selected format from system database 52a, and producing the report on a computer output medium such as VDT 20.

Viewed somewhat differently, the invention includes a computer-assisted process of reporting safety information stored in computer memory. This process includes the step of creating a company database stored in computer memory 14/16. The company database includes a defined list of employees and a defined list of types of incidents. The process also includes the steps of selecting an employee from the company database, selecting a type of incident from the company database, and creating an incident database stored in computer memory by inserting the selected employee and type of incident into a data record. The process next includes the steps of formatting the incident database into a report and producing the report on a computer output medium.

Viewed still differently, the invention includes a computer-aided process of producing incident reports, the process comprising the step of creating a system database 52a stored in computer memory 14/16. System database 52a includes a plurality of defined lists of entries for selected variables and a plurality of defined formats for selected incident reports. The process further comprises the step of creating an incident database 52b stored in computer memory 14/16 by selecting an entry from one or more of the defined lists in system database 52a, and inserting the selected entry or entries into a data record. The process further comprises the step of creating an incident report, by selecting one of the defined formats from system database 52a, extracting and manipulating information from incident database 52b as defined in the selected format, and producing the report on a computer output medium.

Described differently, the invention includes an incident reporting system 10. The reporting system comprises a system database 52a stored in computer memory 14/16, including a plurality of defined lists of system records of selected variables, and a plurality of defined report formats for producing selected incident reports. A system record selector 86 is provided for selecting one or more of the defined system records, and an information extractor 88 is provided for extracting one or more elements from the selected system record.

The reporting system 10 further comprises an incident database 52b stored in computer memory 14/16, including one or more defined lists of incident records of data. Each incident record describes one or more aspect of a specific incident, and may contain one or more of the extracted elements from system database 52a. A report format selector 96 is provided for selecting one or more of the defined report formats, and a report formatter 98 is provided for extracting and manipulating information from incident database 52b as defined in the selected report format. The reporting system 10 further comprises a computer output medium through which the extracted and manipulated information is produced in the selected report format.

Reporting system 10 further comprises an input form database 52a2/52b2 including a plurality of defined input forms for prompting a user for input to system/incident database 52. An input form selector 78 is provided for selecting one or more of the defined input forms, and an input form formatter 80 is provided for extracting and manipulating information from system database 52*a* as defined in the selected input form. A user interface is provided for displaying the selected input form and allowing a user to input information into one or more records of one or more lists of system database 52*a* through the selected input form.

INDUSTRIAL APPLICABILITY

The present invention is particularly applicable to the administration and support of the industry process known as light duty/restricted duty/recurrence of injury recording, analysis and reporting.

I claim:

1. A computer-implemented process of reporting safety information, comprising the steps of:

creating a system database stored in computer memory, the system database including a plurality of defined lists of entries for selected variables and a plurality of defined formats for selected incident reports;

creating an incident database stored in computer memory by selecting an entry from one or more of the defined lists in the system database, and inserting the selected entry or entries into a data record; and creating an incident report by:

selecting one of the defined formats from the system database;

extracting and manipulating information from the incident database as defined in the selected format;

producing the report on a computer output medium; and wherein the plurality of defined formats include an OSHA report 200.

* * * * *